US006852458B2

(12) United States Patent
Ohkura et al.

(10) Patent No.: US 6,852,458 B2
(45) Date of Patent: Feb. 8, 2005

(54) ELECTROPHOTOGRAPHIC PHOTORECEPTOR, AND ELECTROPHOTOGRAPHIC APPARATUS USING THE SAME

(75) Inventors: Kenichi Ohkura, Nagano (JP); Yoshihiro Ueno, Nagano (JP); Masami Kuroda, Kanagawa (JP); Nobuyuki Sekine, Kanagawa (JP)

(73) Assignee: Fuji Electric Imaging Device Co., Ltd., Nagano (JP)

(*) Notice: Subject to any disclaimer, the term of this patent is extended or adjusted under 35 U.S.C. 154(b) by 0 days.

(21) Appl. No.: 10/357,491

(22) Filed: Feb. 4, 2003

(65) Prior Publication Data

US 2003/0219664 A1 Nov. 27, 2003

(30) Foreign Application Priority Data

Feb. 4, 2002 (JP) .................................. 2002-027236

(51) Int. Cl.[7] .............................................. G03G 5/06
(52) U.S. Cl. ..................................... 430/75; 430/58.15
(58) Field of Search ............................. 430/75, 58.15; 399/159

(56) References Cited

U.S. PATENT DOCUMENTS

| 4,963,449 | A | * | 10/1990 | Tanaka et al. | ............ | 430/58.15 |
| 5,252,416 | A | * | 10/1993 | Kuroda et al. | ............ | 430/58.15 |
| 6,383,698 | B1 | * | 5/2002 | Okada et al. | ............ | 430/58.25 |

FOREIGN PATENT DOCUMENTS

| JP | 1-206349 | 8/1989 |
| JP | 1-230054 | 9/1989 |
| JP | 3-290666 | 12/1991 |
| JP | 04-338760 | 11/1992 |
| JP | 4-360148 | 12/1992 |
| JP | 5-092936 | 4/1993 |
| JP | 05-150481 | 6/1993 |
| JP | 5-279582 | 10/1993 |
| JP | 6-130688 | 5/1994 |
| JP | 07-179775 | 7/1995 |
| JP | 8-209023 | 8/1996 |
| JP | 8-278643 | 10/1996 |
| JP | 9-151157 | 6/1997 |
| JP | 9-281728 | 10/1997 |
| JP | 9-281729 | 10/1997 |
| JP | 10-73937 | 3/1998 |
| JP | 10-239874 | 9/1998 |
| JP | 2000-75520 | 3/2000 |
| JP | 2000-143607 | 5/2000 |
| JP | 2000-199979 | 7/2000 |
| JP | 2000-204083 | 7/2000 |
| JP | 2000-314969 | 11/2000 |
| JP | 2000-314970 | 11/2000 |
| JP | 2001-142239 | 5/2001 |
| JP | 2001-222122 | 8/2001 |
| JP | 2001-228637 | 8/2001 |
| JP | 2001-330972 | 11/2001 |
| JP | 2002-37755 | 2/2002 |

OTHER PUBLICATIONS

Tatsushi Kobayashi et al., "Development of Organic Electron Transport Materials", pp. 173–176, (1992).
Yasufumi Mizuta et al., Synthesis and Xerographic Properties of Novel Naphthoquinone, pp. 21–24, (1997).
Hideki Okada et al., Synthesis and Properties of a Novel Electron Transporting Compound, 3,3'-dialkyl-4,4'-bis-naphthylquinone (DBNQ), pp. 207–210, (1998).
Yasuhiro Yamaguchi, et al., Application of Unsymmetrical Diphenoquinone Derivatives to Xerography (1) Molecular Design of a Novel Class of Polymer–dispersible Electron–transport–active Compounds, pp. 266–273, (7.2. 1991).
Yuji Miyahara, Facile Synthesis of 2,5–Diacylthiophenes, pp. 1147–1151, (Sep. 1979).
U.S. Appl. No. 10/357,504, filed Feb. 4, 2003, Kenichi Ohkura et al., Fuji Electric Imaging Device Co., Ltd.

* cited by examiner

Primary Examiner—John L Goodrow

(57) ABSTRACT

An electrophotographic photoreceptor has excellent electrical properties and is stable even upon repeated use. An electrophotographic apparatus using the electrophotographic photoreceptor uses a compound having an excellent electron transporting ability in a photosensitive layer of the electrophotographic photoreceptor. An electrophotographic photoreceptor, in which a photosensitive layer is located on an electrically conductive substrate either directly or via an undercoat layer, contains a compound having a structure represented by the general formula (I).

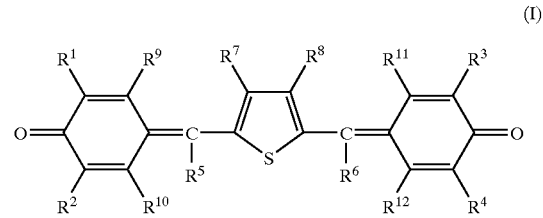

(I)

An electrophotographic apparatus contains the above-mentioned electrophotographic photoreceptor, and carries out a charging process through a positive charging process.

28 Claims, 6 Drawing Sheets

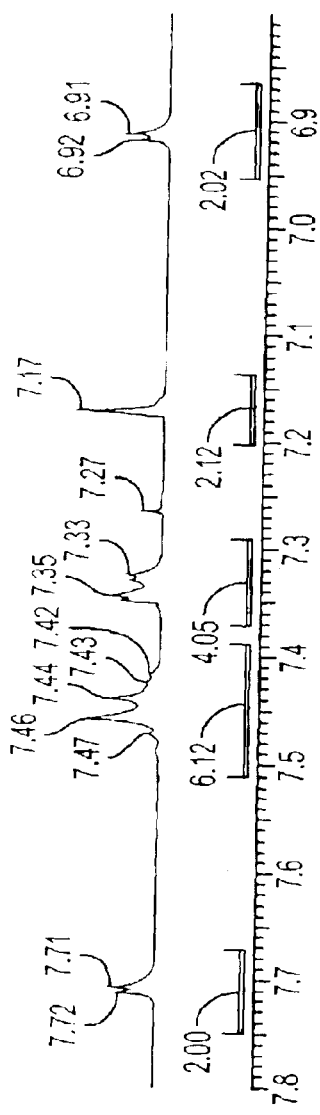
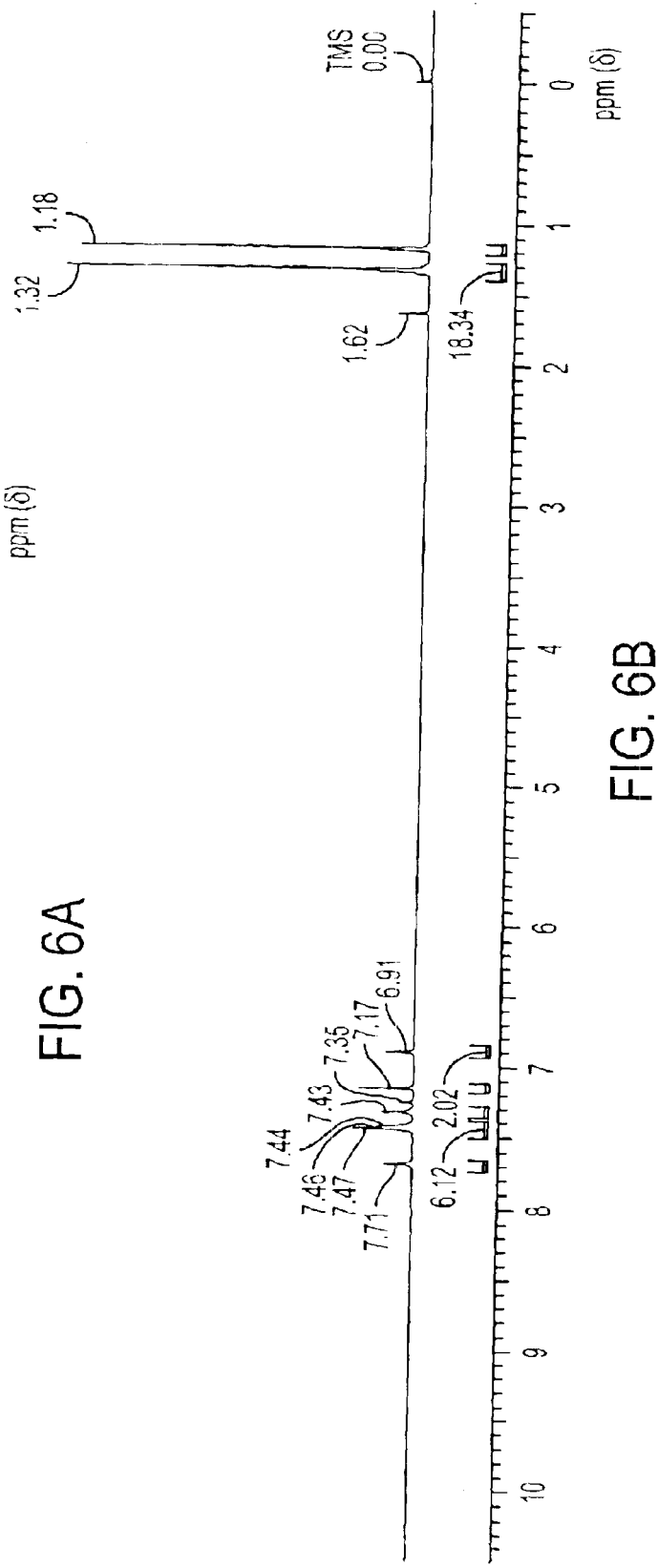
FIG. 6A
FIG. 6B

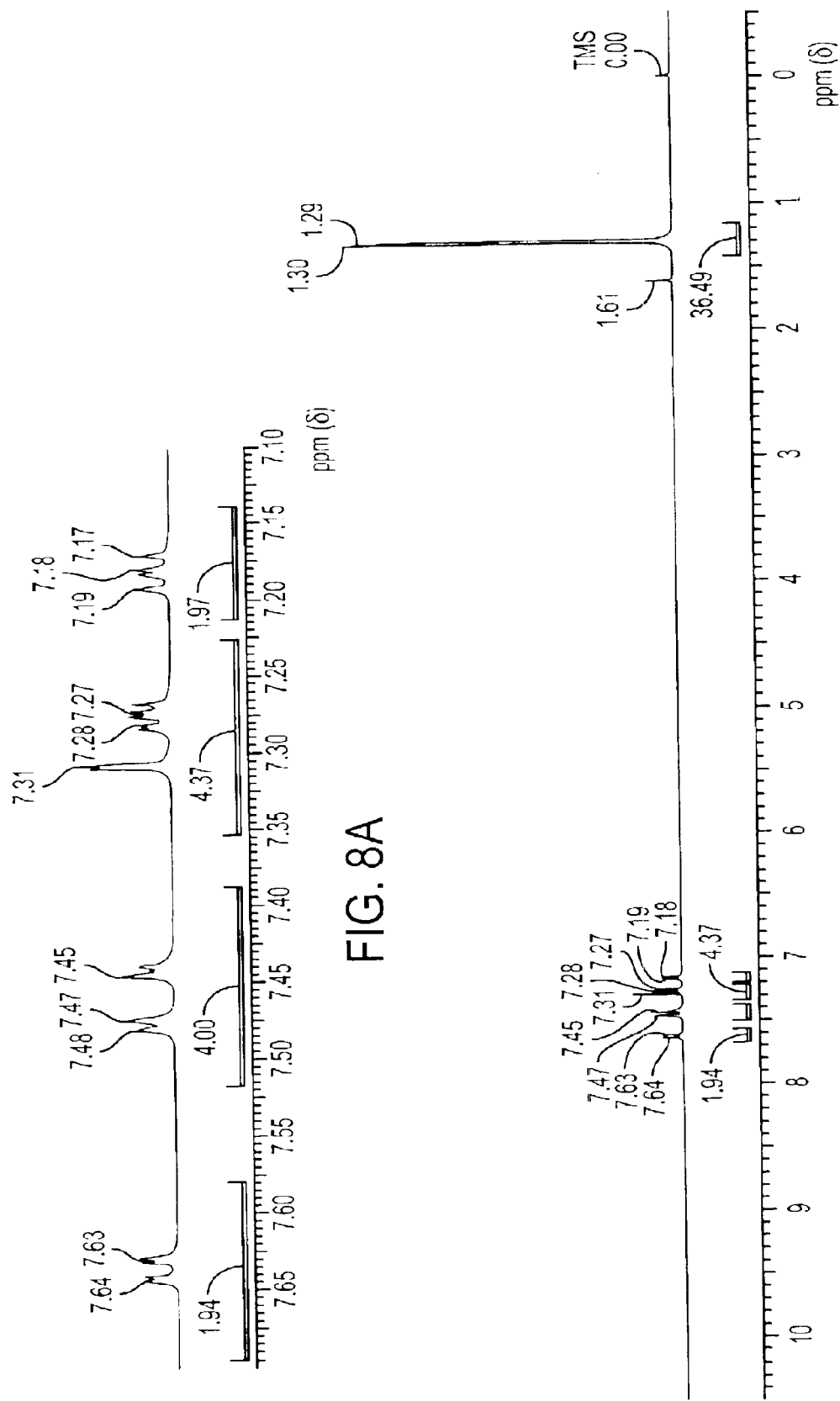

ELECTROPHOTOGRAPHIC PHOTORECEPTOR, AND ELECTROPHOTOGRAPHIC APPARATUS USING THE SAME

CROSS-REFERENCE TO RELATED APPLICATIONS

This application claims the benefit of Japanese Application No. 2002-027236, filed Feb. 4, 2002 in the Japanese Patent Office, the disclosure of which is incorporated herein by reference.

BACKGROUND OF THE INVENTION

1. Field of the Invention

The present invention relates to an electrophotographic photoreceptor (hereinafter referred to as a 'photoreceptor') that uses a specified electron transport substance, and an electrophotographic apparatus using the electrophotographic photoreceptor.

2. Description of the Related Art

In recent years, many organic electrophotographic photoreceptors that use an organic photoconductive material have been proposed and put into practical use as electrophotographic photoreceptors, since organic electrophotographic photoreceptors are non-polluting, are low in cost, and since the photoreceptor properties may be variously designed due to the degree of freedom of material selection.

The photosensitive layer of an organic electrophotographic photoreceptor predominantly comprises a layer in which an organic photoconductive material is dispersed in a resin. Many structures have been proposed, for example, a layered-type structure in which a layer in which a charge generation material is dispersed in a resin (charge generation layer) and a layer in which a charge transport material is dispersed in a resin (charge transport layer) are laminated sequentially. Also, a single layer type structure has been proposed, comprising a single layer in which a charge generation material and a charge transport material are dispersed together in a resin.

Of the above, a functionally separated, layered type photoreceptor, in which a charge transport layer is laminated on top of a charge generation layer as the photosensitive layer, has excellent photoreceptor properties and durability, and hence has been widely put into practical use. A hole transport material is generally used as the charge transport material in the charge transport layer of the functionally separated layered type photoreceptor, and hence such a photoreceptor is used in an electrophotographic apparatus that operates with a negative charging process. However, the negative corona discharge used in the negative charging process is unstable compared with a positive corona discharge, and moreover, the amount of ozone generated is large. Hence, there have been problems of adverse effects on the photoreceptor and adverse effects on the usage environment. An organic electrophotographic photoreceptor that can be used with a positive charging process would be effective for resolving such problems.

To make a photoreceptor having excellent durability, as described above, which would be suitable for a positive charging process and have high sensitivity, it is necessary to use a substance having an excellent electron transporting function. Many such substances and photoreceptors using such substances have been proposed. For example, in Japanese Patent Application Laid-open No. 1-206349, Japanese Patent Application Laid-open No. 4-360148, Journal of the Society of Electrophotography of Japan, Vol. 30, p266 to 273(1991), Japanese Patent Application Laid-open No. 3-290666, Japanese Patent Application Laid-open No. 5-92936, Proceedings of the Pan-Pacific Imaging Conference/Japan Hardcopy '98, Jul. 15 to 17, 1998, J A Hall, Tokyo, Japan, p207 to 210, Japanese Patent Application Laid-open No. 9-151157, Papers from Japan Hardcopy '97, Jul. 9 to 11, 1997, J A Hall (Otemachi, Tokyo), p21 to 24, Japanese Patent Application Laid-open No. 5-279582, Japanese Patent Application Laid-open No. 7-179775, Papers from Japan Hardcopy '92, Jul. 6 to 8, 1992, J A Hall (Otemachi, Tokyo), p173 to 176, Japanese Patent Application Laid-open No. 10-73937, Japanese Patent Application Laid-open No. 1-230054, Japanese Patent Application Laid-open No. 8-278643, Japanese Patent Application Laid-open No. 9-190002, Japanese Patent Application Laid-open No. 9-190003, and Japanese Patent Application Laid-open No. 2001-222122, many electron transport substances and electrophotographic photoreceptors using such electron transport substances are proposed and disclosed, and have received attention. Moreover, in the case of a single layer type photosensitive layer, photoreceptors that use a combination of an electron transport substance and a hole transport substance have been disclosed, for example, in Japanese Patent Application Laid-open No. 5-150481, Japanese Patent Application Laid-open No. 6-130688, Japanese Patent Application Laid-open No. 9-281728, Japanese Patent Application Laid-open No. 9-281729, and Japanese Patent Application Laid-open No. 10-239874. have received attention as having high sensitivity, and have been put into practical use in some cases.

Moreover, in the search for photoreceptors having yet better properties, the present inventors have also proposed various photoreceptors that contain a substance having an electron transporting function (disclosed, for example, in Japanese Patent Application Laid-open No. 2000-75520, Japanese Patent Application Laid-open No. 2000-199979, Japanese Patent Application Laid-open No. 2000-143607, and Japanese Patent Application Laid-open No. 2001-142239).

However, with diphenoquinone compounds and stilbenequinone compounds that are already known as substances having an electron transporting function, electrical properties such as residual potential and sensitivity are not sufficiently satisfactory. Hence, there have been aspirations to realize electrophotographic photoreceptors and electrophotographic apparatuses of higher performance by using an electron transport substance having better electrical properties.

SUMMARY OF THE INVENTION

It is thus an aspect of the present invention to provide an electrophotographic photoreceptor that has excellent electrical properties and is stable even upon repeated use, and an electrophotographic apparatus using this electrophotographic photoreceptor, by using a compound having an excellent electron transporting ability in an electrophotographic photoreceptor that has a photosensitive layer on an electrically conductive substrate.

Additional aspects and/or advantages of the invention will be set forth in part in the description which follows and, in part, will be obvious from description, or may be learned by practice of the invention.

To attain aspects and/or advantages of the invention, an electrophotographic photoreceptor comprises an electrophotographic photoreceptor in which a photosensitive layer is provided on an electrically conductive substrate either directly or via an undercoat layer, wherein the photosensitive layer contains a compound having a structure represented by the below-mentioned general formula (I):

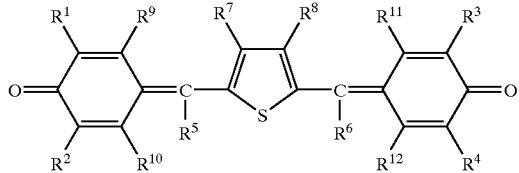

wherein $R^1$ to $R^4$ and $R^9$ to $R^{12}$ are the same or different and each represents a hydrogen atom, an optionally substituted alkyl group having 1 to 12 carbon atoms, an optionally substituted cyclic alkyl group, an optionally substituted aryl group, or an alkoxy group having 1 to 6 carbon atoms; $R^5$ and $R^6$ are the same or different and each represents a hydrogen atom, an optionally substituted alkyl group having 1 to 12 carbon atoms, an optionally substituted aryl group, or an optionally substituted heterocyclic group; $R^7$ and $R^8$ are the same or different and each represents a hydrogen atom, an optionally substituted alkyl group having 1 to 12 carbon atoms, an optionally substituted aryl group, or an alkoxy group having 1 to 6 carbon atoms; and each of the optional substituents is a halogen atom, an alkyl group having 1 to 6 carbon atoms, an alkoxy group having 1 to 6 carbon atoms, an aryl group, or a heterocyclic group.

According to embodiments of the present invention, in the case of an electrophotographic photoreceptor in which a photosensitive layer is provided on an electrically conductive substrate, by making the photosensitive layer of the photoreceptor contain a specified compound having an electron transporting ability as an electron transport substance, an effect is produced whereby the electron transporting ability is improved, and hence excellent electrical properties are exhibited. Moreover, there is little trapping of charge, and thus stability is excellent even upon repeated use.

The photoreceptor, according to embodiments of the present invention, may be a single layer type photoreceptor in which the photosensitive layer is a single layer type photosensitive layer. In particular, such a photoreceptor can be suitably applied to an electrophotographic apparatus that carries out a charging process through a positive charging process.

With the photoreceptor according to embodiments of the present invention, for example, a publicly known hole transport substance, such as one disclosed in Japanese Patent Application Laid-open No. 2000-314969, can be used as a hole transport substance in the photosensitive layer. In particular, a styryl compound may be used.

Moreover, with the photoreceptor according to embodiments of the present invention, a publicly known charge generation substance can be used as a charge generation substance in the photosensitive layer. In particular, a phthalocyanine compound may be used. As phthalocyanine compounds, for example, an X-type non-metal phthalocyanine, α-type titanyl phthalocyanine, a Y-type titanyl phthalocyanine disclosed in Japanese Patent Application Laid-open No. 2001-228637, a titanyl phthalocyanine according to the invention disclosed in Japanese Patent Application Laid-open No. 2001-330972, may be used, although there is no limitation to said compounds with the present invention.

Moreover, an electrophotographic apparatus according to embodiments of the present invention contains an electrophotographic photoreceptor as described above, and carries out a charging process through a positive charging process.

BRIEF DESCRIPTION OF THE DRAWINGS

These and other aspects and advantages of the invention will become apparent and more readily appreciated from the following description of the preferred embodiments, taken in conjunction with the accompanying drawings of which:

FIGS. 6A–6B show the $^1$H-NMR spectrum of the compound represented by structural formula I-21;

FIGS. 8A–8B show the $^1$H-NMR spectrum of the compound represented by structural formula I-51.

DETAILED DESCRIPTION OF THE PREFERRED EMBODIMENTS

Figure 1:
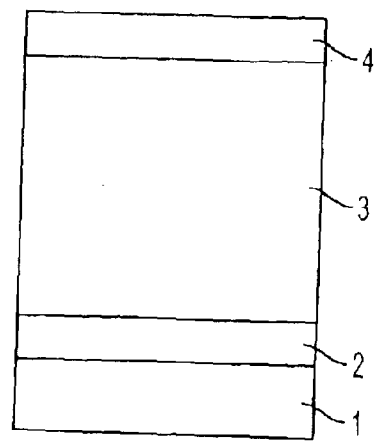
FIG. 1 is a schematic sectional view illustrating an electrophotographic photoreceptor according to an embodiment of the invention.

Reference will now be made in detail to the present preferred embodiments of the present invention, examples of which are illustrated in the accompanying drawings, wherein like reference numerals refer to the like elements throughout. The embodiments are described below in order to explain the present invention by referring to the Figures.

A compound according to embodiments of the present invention represented by above-mentioned general formula (I) can be synthesized, for example, in accordance with the below-mentioned reaction formula (1). Note that in the below-mentioned reaction formula, TMS represents a trimethylsilyl group, and TBAF represents tetrabutylammonium fluoride.

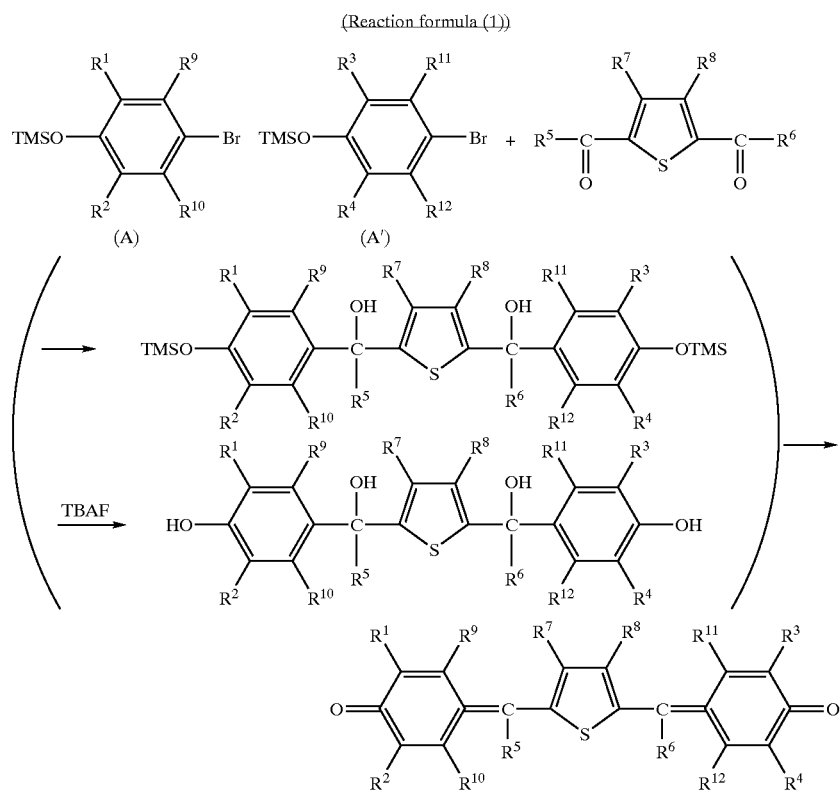
Specific examples of the compound represented by above-mentioned general formula (I) are shown below, but there is no limitation to said compounds in the present invention. Note that the substituent '+' in the specific examples below represents a t-butyl group.
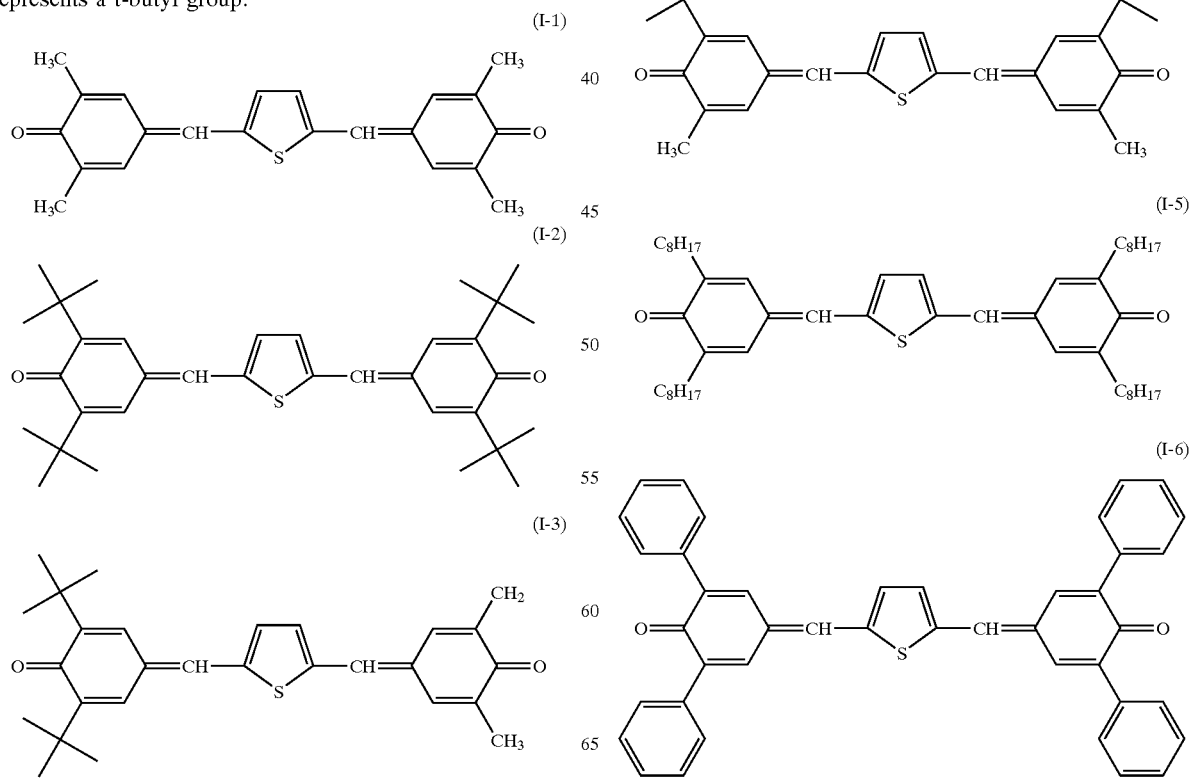

(I-7)
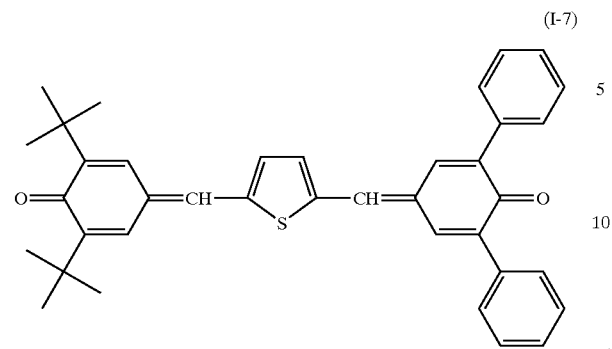
(I-8)
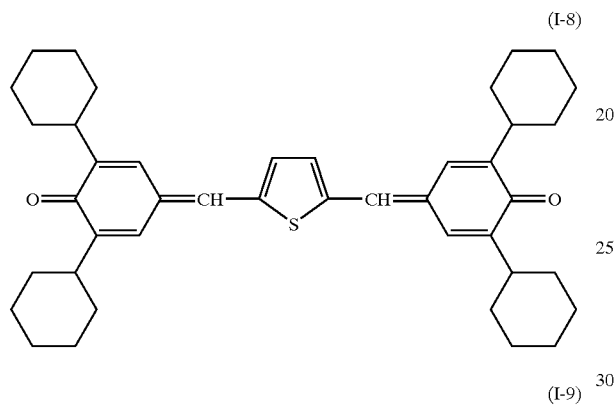
(I-9)
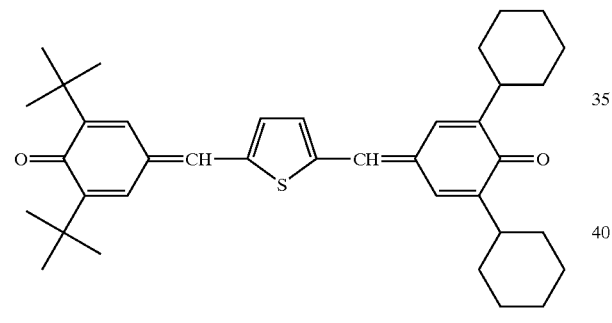
(I-10)
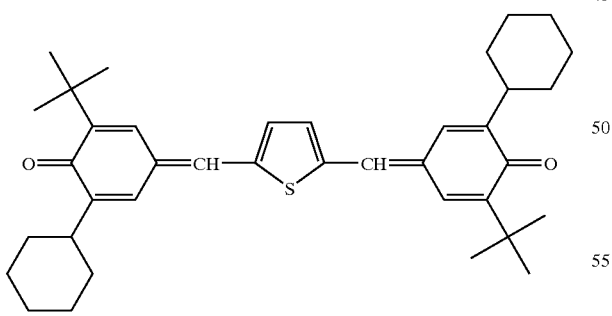
(I-11)
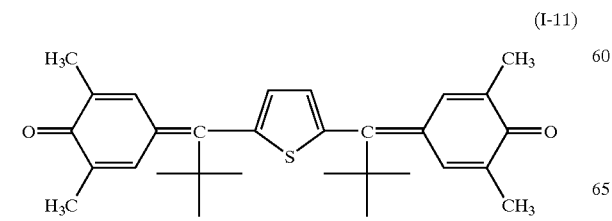
(I-12)
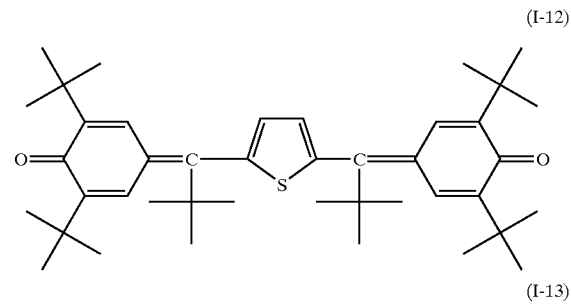
(I-13)
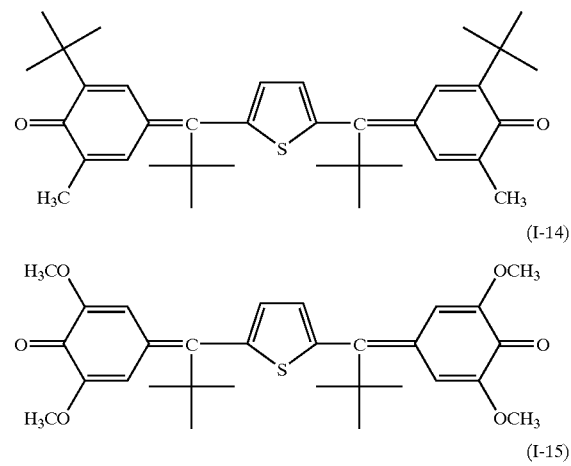
(I-14)
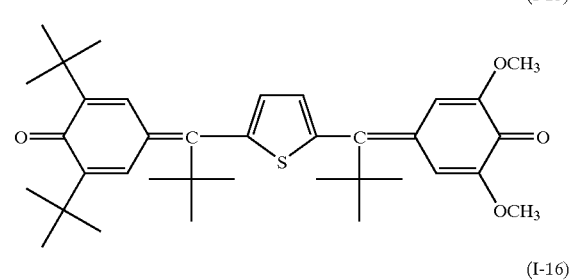
(I-15)
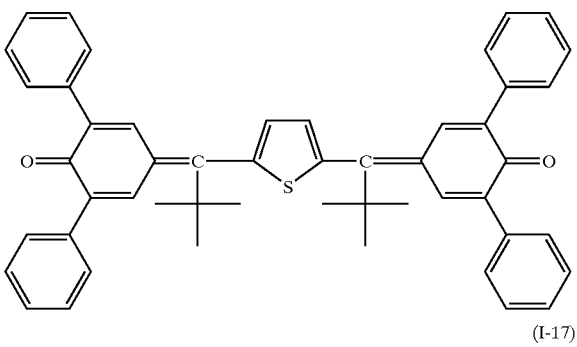
(I-16)
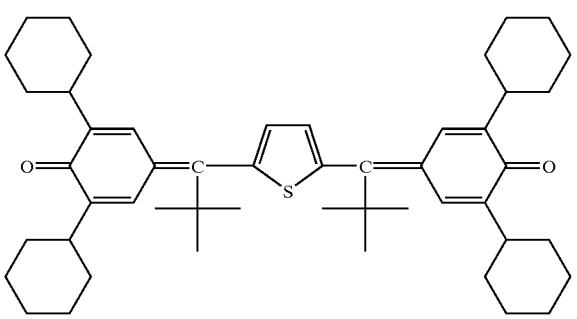
(I-17)

(I-18)
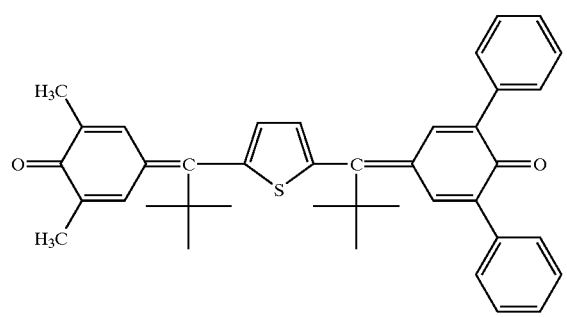
(I-19)
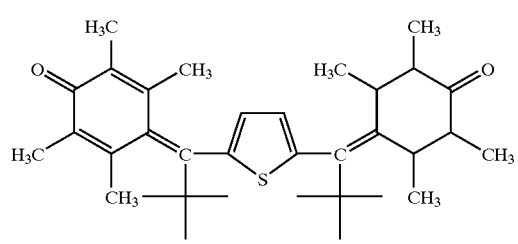
(I-20)
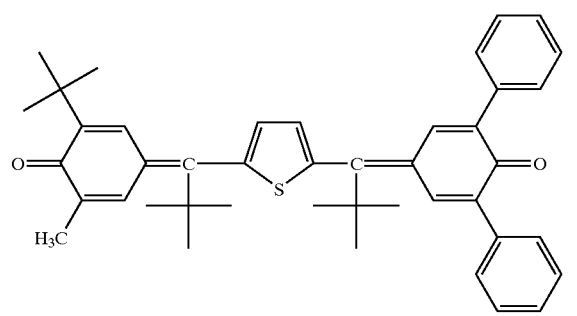
(I-21)
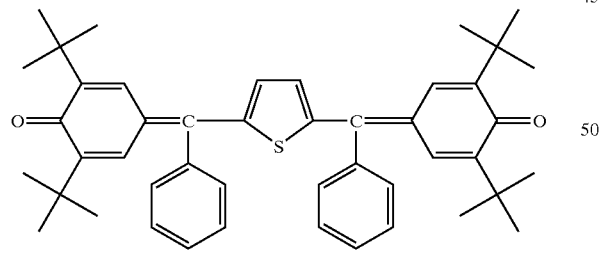
(I-22)
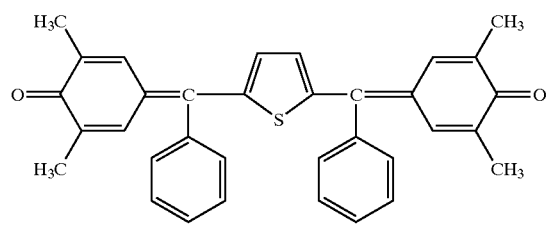
(I-23)
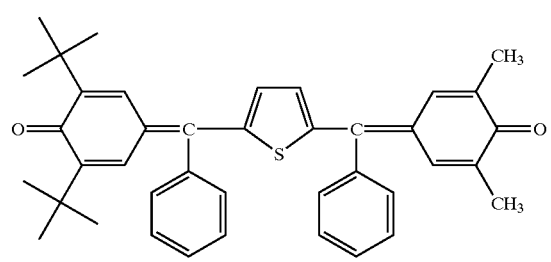
(I-24)
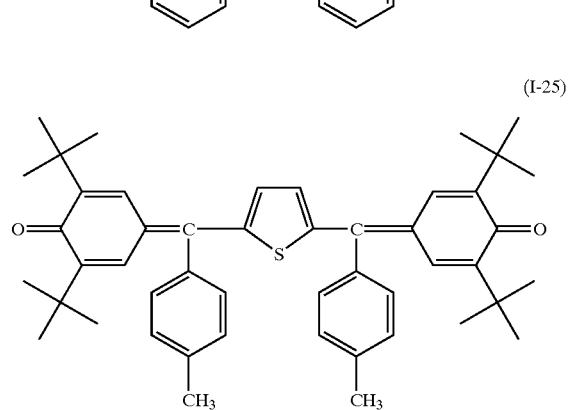
(I-25)
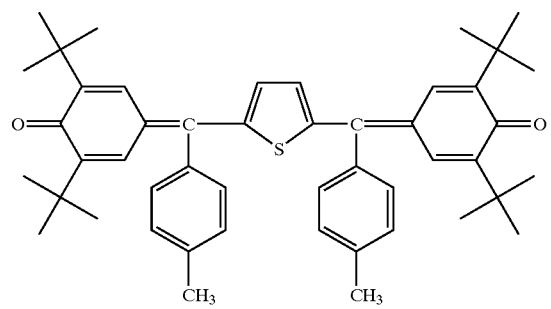
(I-26)
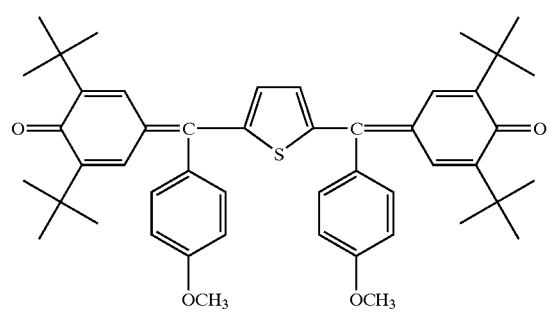
(I-27)
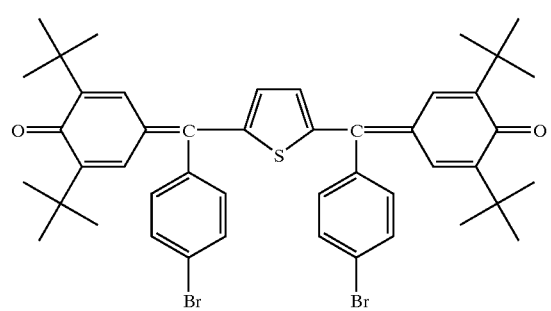

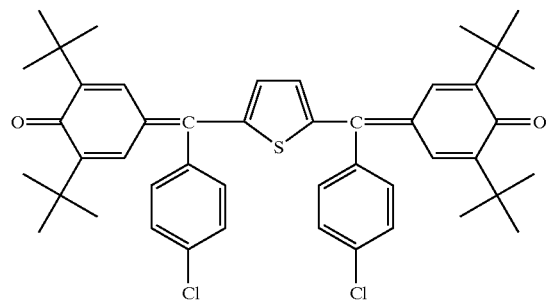
(I-28)
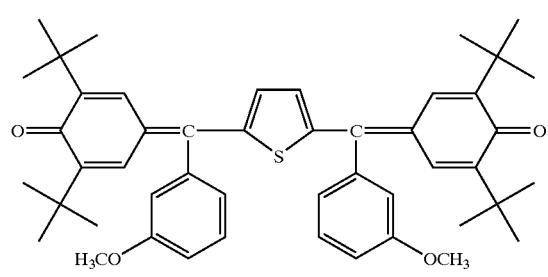
(I-29)
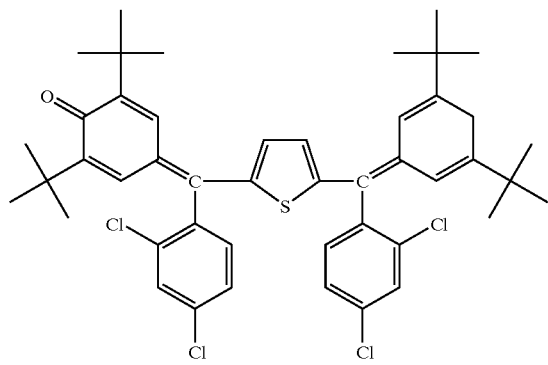
(I-30)
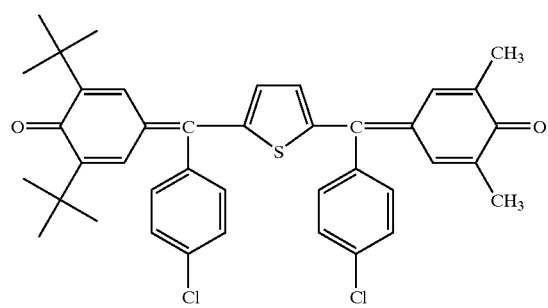
(I-31)
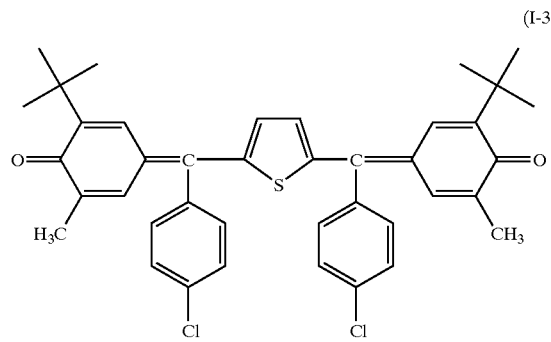
(I-32)
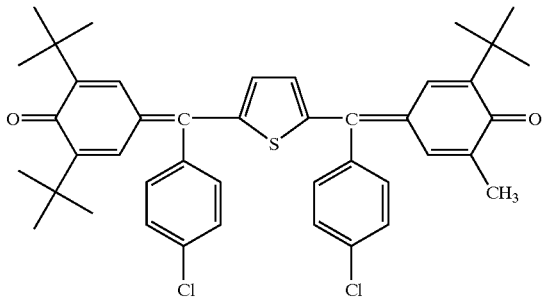
(I-33)
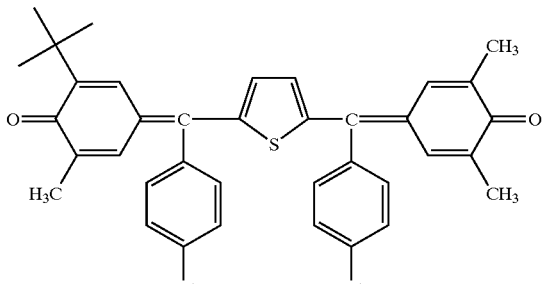
(I-34)
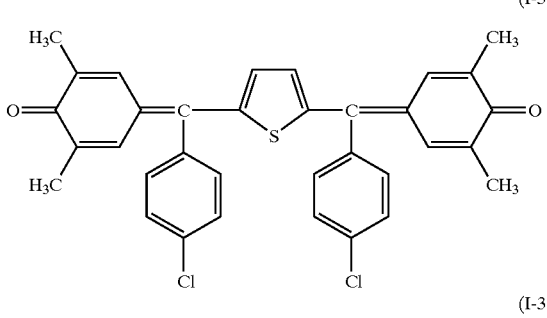
(I-35)
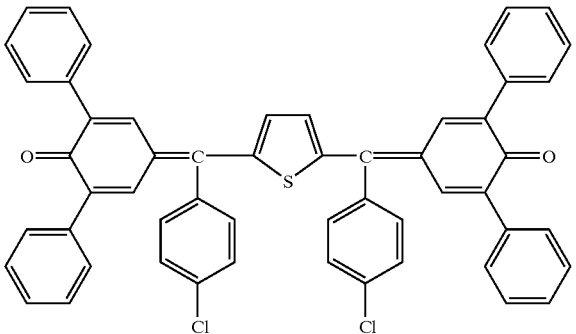
(I-36)
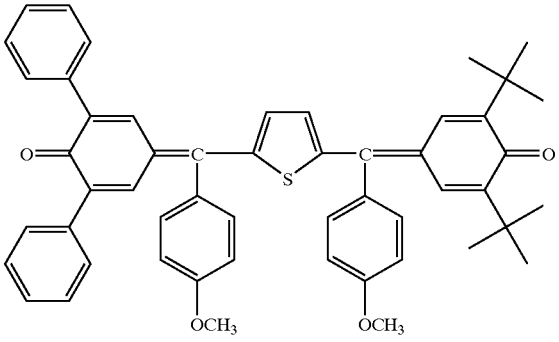
(I-37)

(I-38)
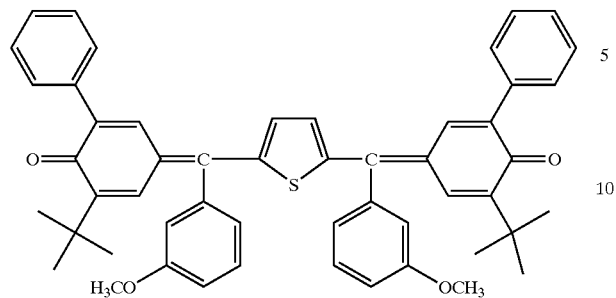
(I-39)
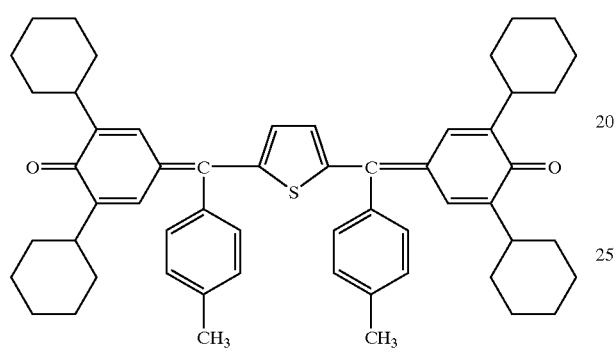
(I-40)
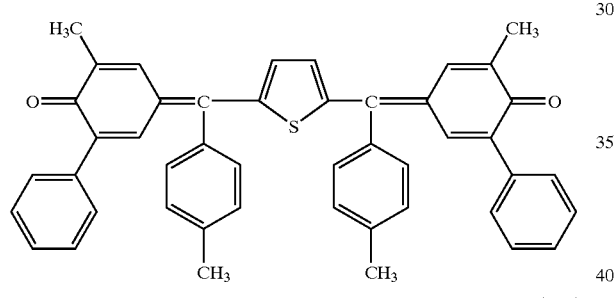
(I-41)
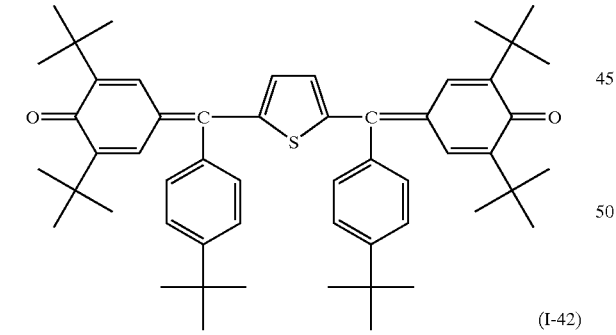
(I-42)
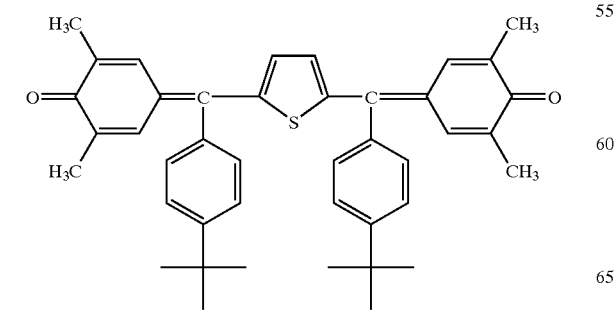
(I-43)
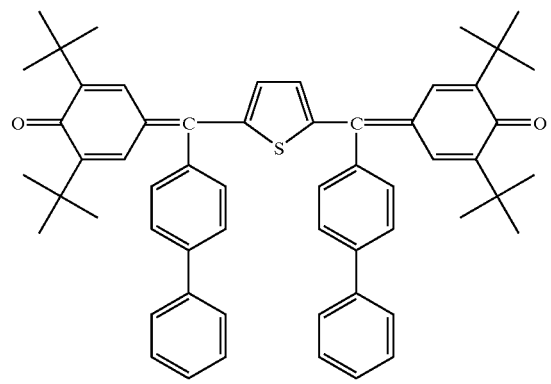
(I-44)
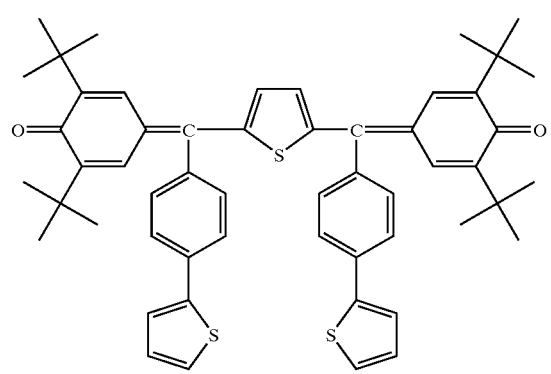
(I-45)
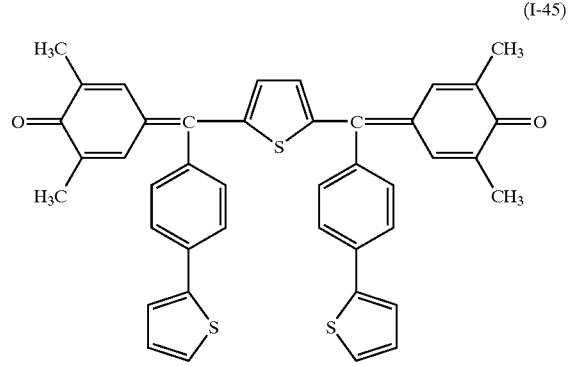
(I-46)
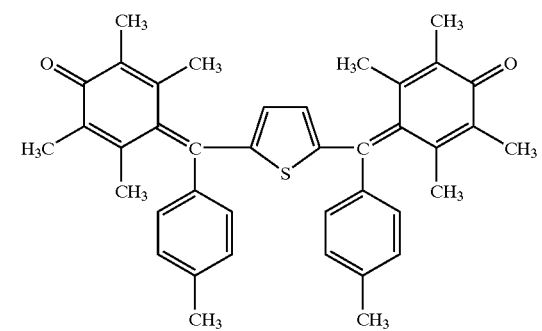

-continued
(I-47)
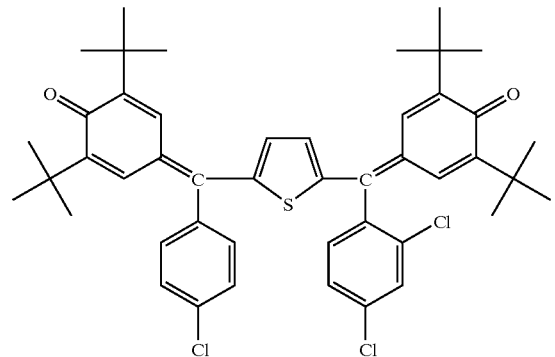
(I-48)
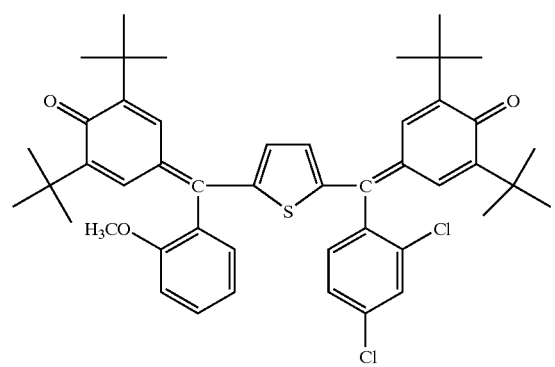
(I-49)
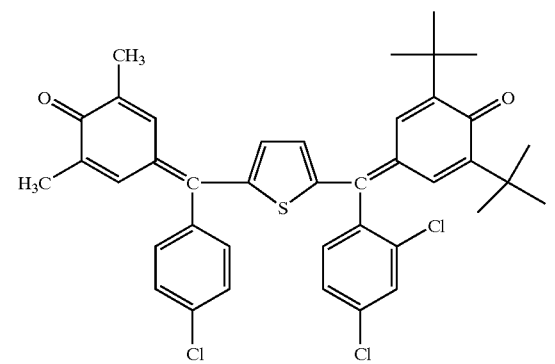
(I-50)
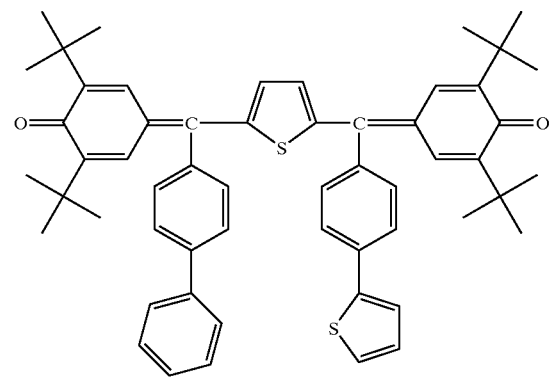
-continued
(I-51)
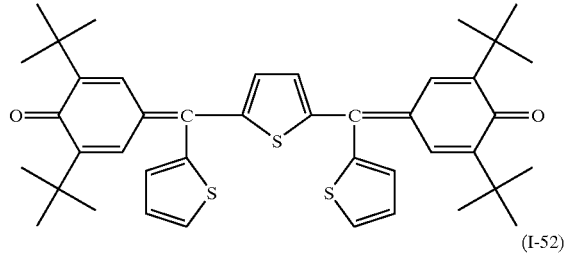
(I-52)
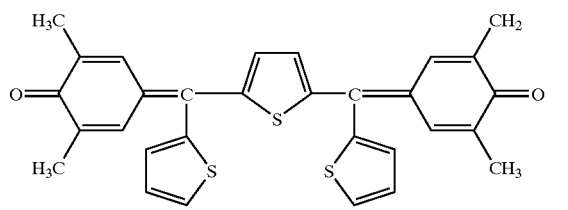
(I-53)
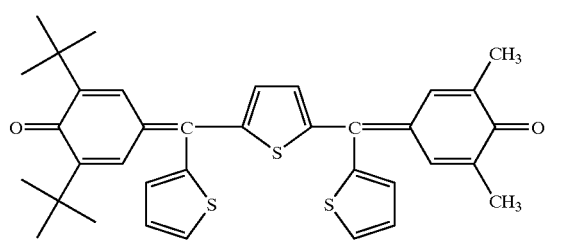
(I-54)
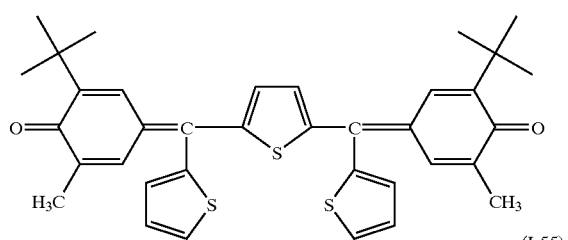
(I-55)
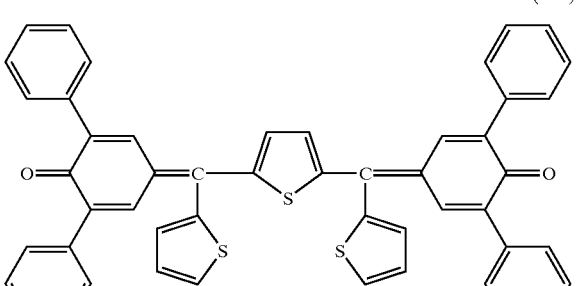
(I-56)
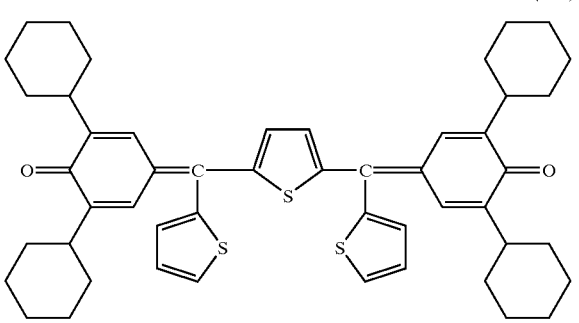

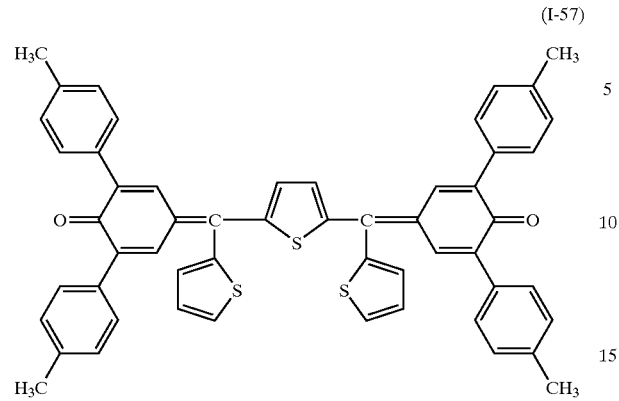
(I-57)
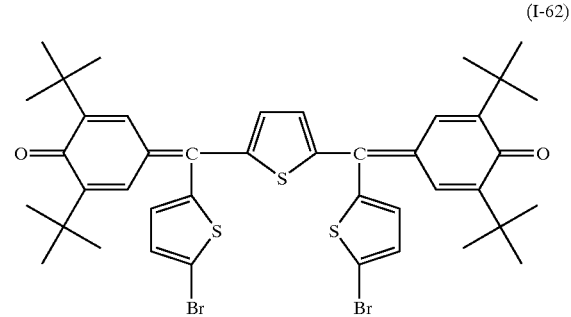
(I-62)
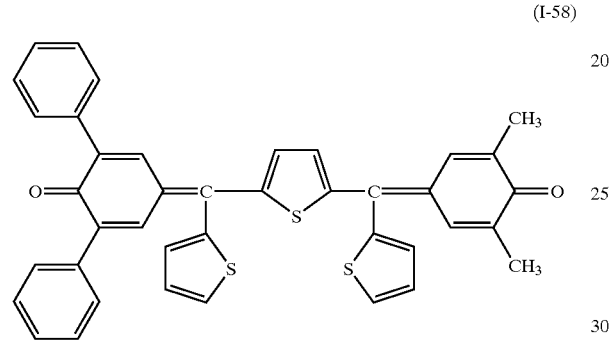
(I-58)
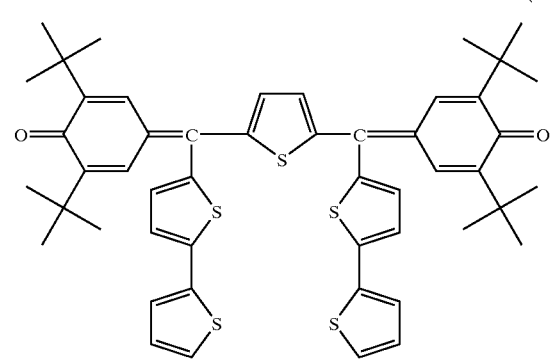
(I-63)
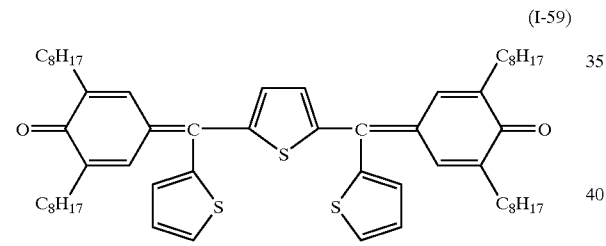
(I-59)
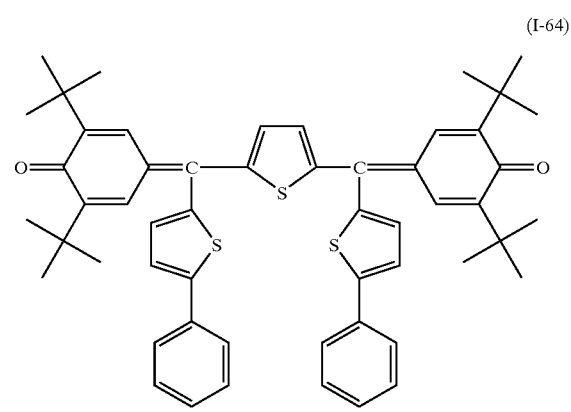
(I-64)
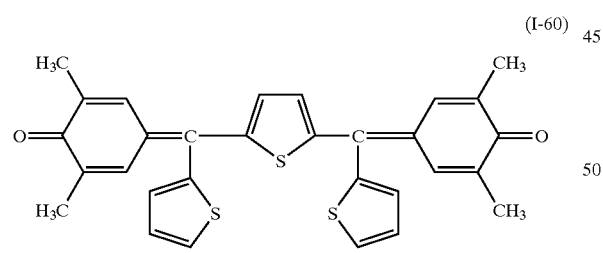
(I-60)
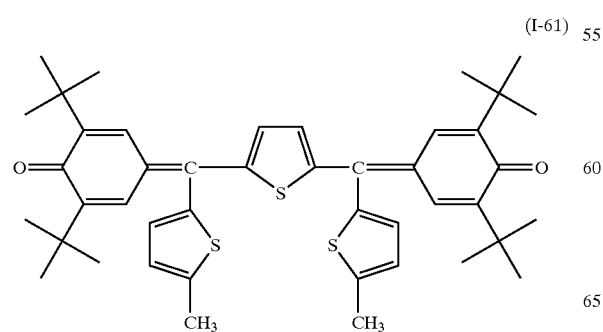
(I-61)
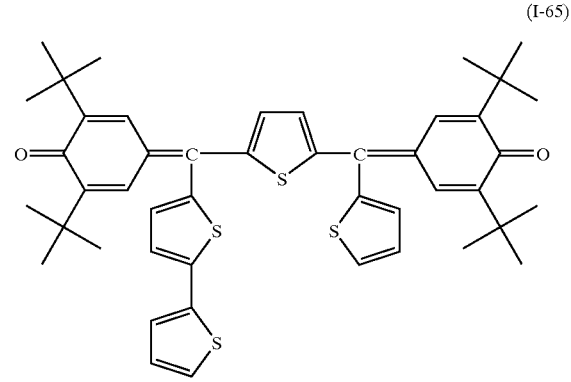
(I-65)

(I-66)
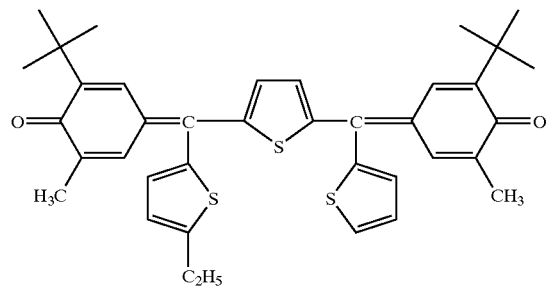
(I-71)
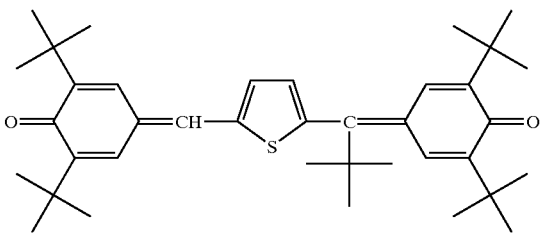
(I-67)
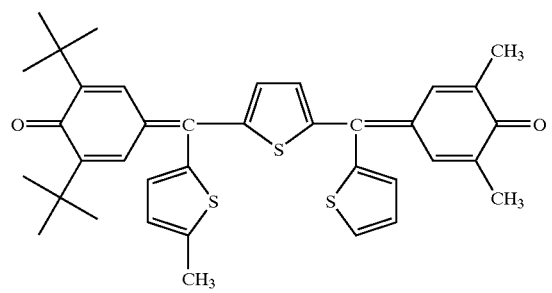
(I-72)
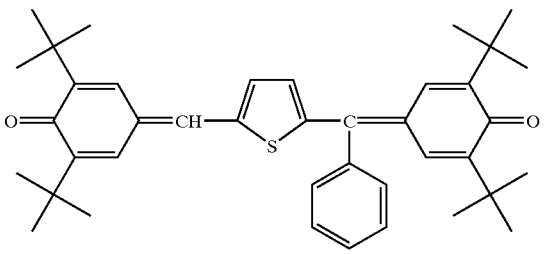
(I-73)
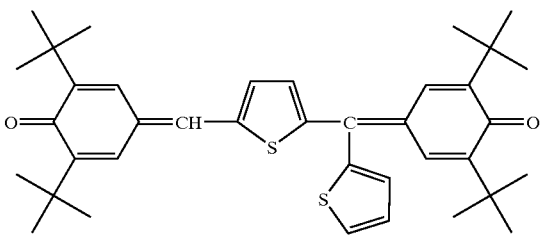
(I-68)
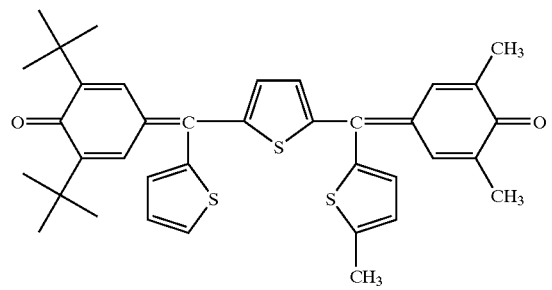
(I-74)
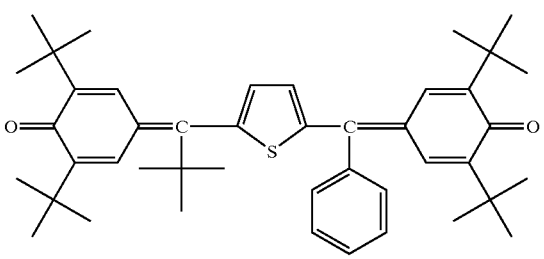
(I-69)
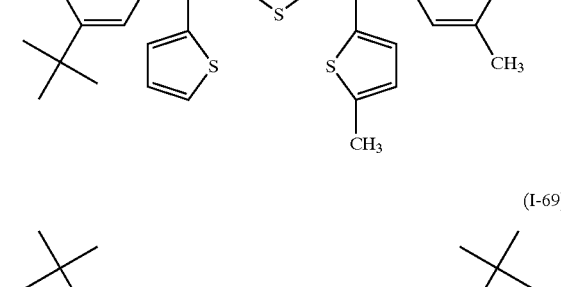
(I-75)
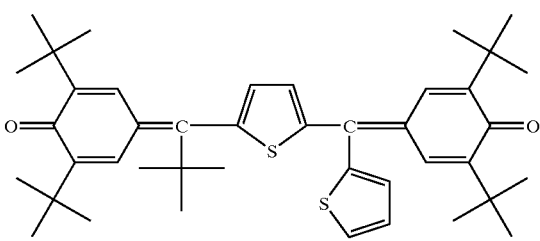
(I-70)
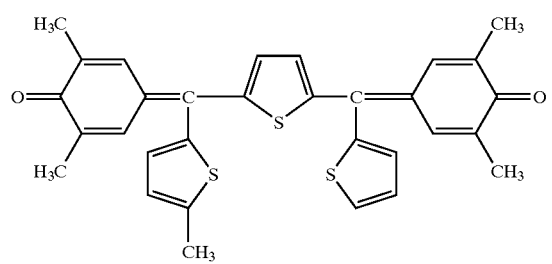
(I-76)

(I-77)

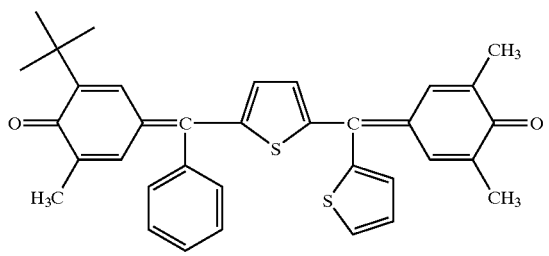

(I-78)

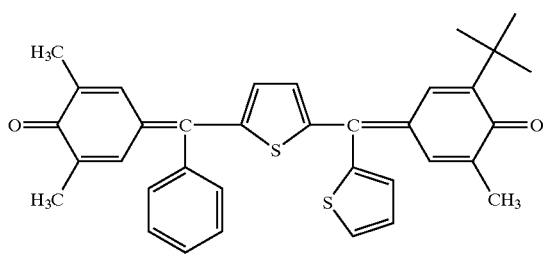

(I-79)

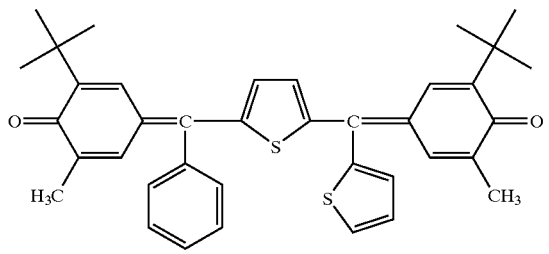

(I-80)

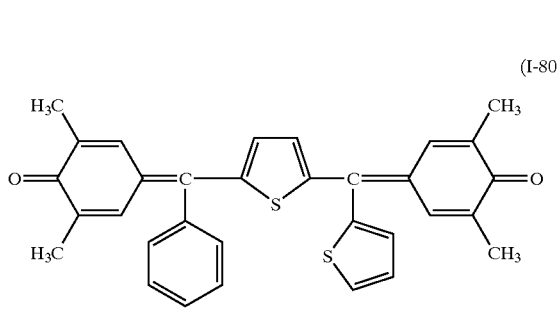

Following is a description of specific embodiments of the electrophotographic photoreceptor of the present invention, with reference to the drawings.

Figure 2:
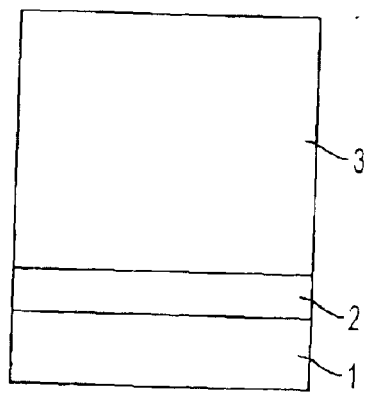
FIG. 2 is a schematic sectional view illustrating an example of a single layer type electrophotographic photoreceptor according to an embodiment of the invention.
Figure 3:
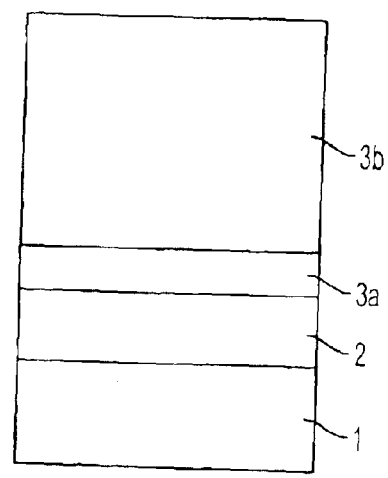
FIG. 3 is a schematic sectional view illustrating an example of a layered type electrophotographic photoreceptor according to an embodiment of the invention.
Figure 4:
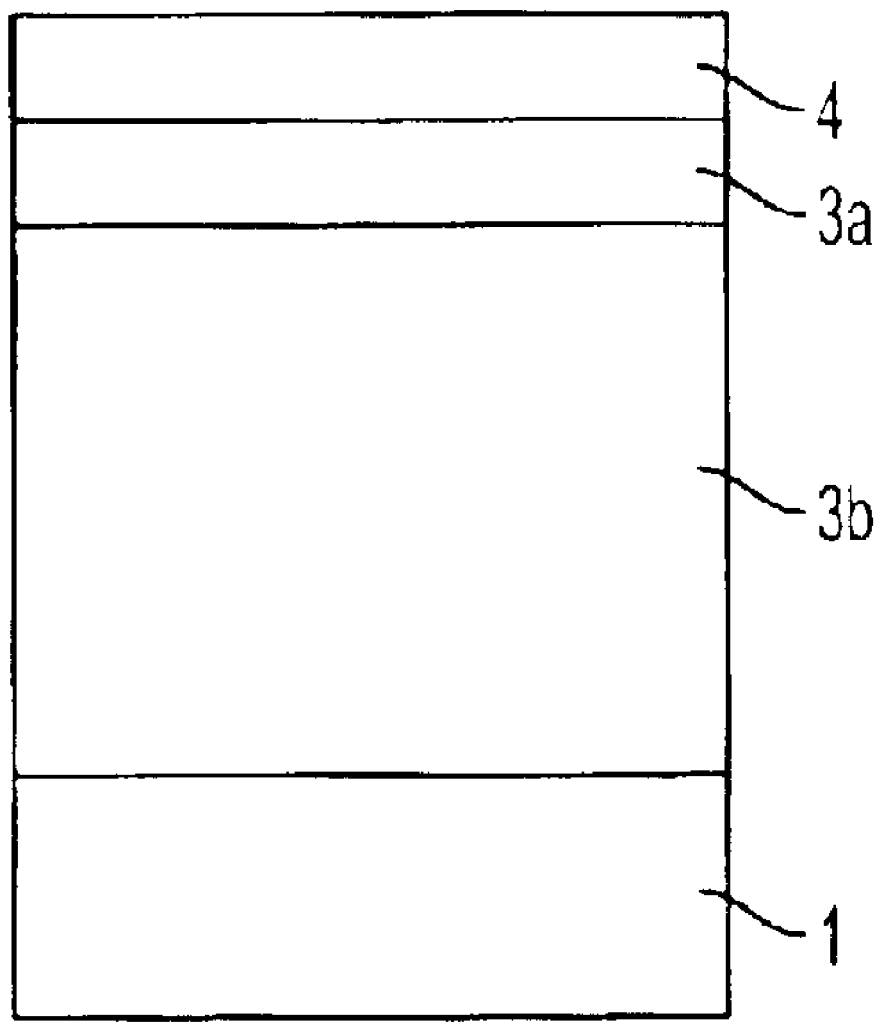
FIG. 4 is a schematic sectional view illustrating another example of a layered type electrophotographic photoreceptor according to an embodiment of the invention.

FIG. 1 is a conceptual sectional view illustrating an example of the photoreceptor according to an embodiment of the present invention comprising an electrically conductive substrate 1, an undercoat layer 2, a photosensitive layer 3, and a protective layer 4 wherein the undercoat layer 2 and the protective layer 4 are provided as necessary. The photosensitive layer 3 may be a single layer type comprising a single layer that has both a charge generating function and a charge transporting function, or may be a functionally separated type in which a charge generation layer and a charge transport layer that are separate from one another are laminated sequentially. Principal specific examples are photoreceptors having the layer structures shown in FIGS. 2–4. FIG. 2 shows a photoreceptor in which the photosensitive layer 3 is the single layer type. FIG. 3 shows a functionally separated layered type photoreceptor in which the photosensitive layer 3 comprises a charge generation layer 3a and a charge transport layer 3b laminated in this order on top of the undercoat layer 2. FIG. 4 shows a functionally separated layered type photoreceptor in which the photosensitive layer 3 comprises a charge transport layer 3b and a charge generation layer 3a laminated in this order, and having a protective layer 4 located thereupon.

The electrically conductive substrate 1 acts as an electrode for the photoreceptor and also acts as a support for the other layers. The electrically conductive substrate 1 may be tube-shaped, plate-shaped or film-shaped, and in terms of the material, may be a metal such as aluminum, stainless steel or nickel, or glass or a resin that has been subjected to electrically conductive treatment.

The undercoat layer 2 is provided as necessary. The undercoat layer 2 comprises a layer having a resin as a principal component thereof, an oxide film such as an alumite film, or the like, and is provided as necessary to prevent the injection of unwanted charge from the electrically conductive substrate into the photosensitive layer, covering defects on the substrate surface, improving the adhesion of the photosensitive layer, or the like. As the resin binder for the undercoat layer, a polycarbonate resin, a polyester resin, a polyvinyl acetal resin, a polyvinyl butyral resin, a vinyl chloride resin, a vinyl acetate resin, polyethylene, polypropylene, polystyrene, an acrylic resin, a polyurethane resin, an epoxy resin, a melamine resin, a silicone resin, a polyamide resin, a polystyrene resin, a polyacetal resin, a polyarylate resin, a polysulfone resin, a methacrylic acid ester polymer, a copolymer of the above, and so on can be used in a suitable combination. Moreover, metal oxides such as silicon oxide (silica), titanium oxide, zinc oxide, calcium oxide, aluminum oxide (alumina) and zirconium oxide, metal sulfides such as barium sulfide and calcium sulfide, metal nitrides such as silicon nitride and aluminum nitride, and metal oxide fine particles may be included in the resin binder.

The thickness of the undercoat layer, while depending on the composition of the undercoat layer, may be set as desired within a range such that there are no adverse effects such as an increase in the residual potential upon repeated continuous use, and is generally about 0.01 μm to 50 μm.

The photosensitive layer 3 predominantly comprises two layers, i.e., a charge generation layer 3a and a charge transport layer 3b for the functionally separated type, and comprises one layer for the single layer type.

The charge generation layer 3a is formed by carrying out vacuum deposition of an inorganic or organic photoconductive substance, or by applying on a material comprising particles of an inorganic or organic photoconductive substance dispersed in a resin binder, and has a function of generating charge upon receiving light. Moreover, it is important that the charge generation efficiency is high, and also that the charge generated is injected into the charge transport layer 3b. Hence, it is preferable for the electric field dependence to be low, with injection being good even with a low electric field.

The charge generation layer need merely have a charge generating function. Hence, the thickness of the charge generation layer is determined by the optical absorption coefficient of the charge generation substance, but is generally not more than 5 μm, and preferably is not more than 1 μm.

The charge generation layer has the charge generation substance as a principal component thereof, but the charge generation substance can also be used with a charge transport substance or the like added thereto. A phthalocyanine type pigment, an azo pigment, an anthanthrone pigment, a perylene pigment, a perinone pigment, a squalirium pigment, a thiopyrylium pigment, a quinacridone or the like may be used as the charge generation substance, or such pigments may be used in a suitable combination. In particular, as an azo pigment a disazo pigment or a trisazo pigment is preferable, as a perylene pigment N,N'-bis(3,5-dimethylphenyl)-3,4:9,10-perylene-bis(carboximide) is preferable, and as a phthalocyanine type pigment a non-metal phthalocyanine, a copper phthalocyanine or a titanyl phthalocyanine is preferable.

In the embodiments of the present invention, it is particularly preferable to use a phthalocyanine compound as the charge generation substance. Various crystalline forms of phthalocyanines exist, with X-type non-metal phthalocyanines, τ-type non-metal phthalocyanines, ε-type copper phthalocyanine, α-type titanyl phthalocyanine, β-type titanyl phthalocyanine, Y-type titanyl phthalocyanine, amorphous titanyl phthalocyanine, the titanyl phthalocyanine disclosed in Japanese Patent Application Laid-open No. 8-209023 for which the CuKα:X-ray diffraction spectrum has a maximum peak at a Bragg angle 2θ of 9.6°, being known. Of said substances, the X-type non-metal phthalocyanine, α-type titanyl phthalocyanine, and Y-type titanyl phthalocyanine disclosed, for example, in Japanese Patent Application Laid-open No. 2001-228637, and the titanyl phthalocyanine according to the invention disclosed in Japanese Patent Application Laid-open No. 2001-330972 are particularly preferable.

Moreover, out of the above-mentioned charge generation substances, there are some that have a charge transporting ability as well as a charge generating function. In particular, azo pigments and perylene pigments have an electron transporting ability, and may be used as an electron transport substance as well as for charge generation.

As the resin binder for the charge generation layer, a polyvinyl acetal resin, a polyvinyl butyral resin, a vinyl chloride resin, a vinyl acetate resin, a silicone resin, a polycarbonate resin, a polyester resin, polyethylene, polypropylene, polystyrene, an acrylic resin, a polyurethane resin, an epoxy resin, a melamine resin, a polyamide resin, a polystyrene resin, a polyacetal resin, a polyarylate resin, a polysulfone resin, a methacrylic acid ester polymer, a copolymer of the above, etc., can be used in a suitable combination. Moreover, resins of the same type but having different molecular weights may be used mixed together. The content of the resin binder is 10 to 90 wt %, preferably 20 to 80 wt %, relative to the solid content of the charge generation layer.

The charge transport layer 3b is a coating film comprising a material in which a charge transport material is dispersed in a resin binder. The charge transport layer 3b exhibits a function of holding the charge of the photoreceptor as an insulator layer in a dark place, and transports charge injected from the charge generation layer upon receiving light.

As charge transport substances, there are hole transport substances and electron transport substances, but in the present invention it is necessary to use at least a compound represented by above-mentioned general formula (I) as an electron transport substance. Moreover, in embodiments of the present invention, in addition to compound I, it is possible to use other electron transport substance(s) and/or hole transport substance(s) at the same time.

Publicly known electron transport substance(s) may be used as the other electron transport substance(s). For example, electron acceptors/electron transport substances such as succinic anhydride, maleic anhydride, dibromosuccinic anhydride, phthalic anhydride, 3-nitrophthalic anhydride, 4-nitrophthalic anhydride, pyromellitic anhydride, pyromellitic acid, trimellitic acid, trimellitic anhydride, phthalimide, 4-nitrophthalimide, tetracyanoethylene, tetracyanoquinodimethane, chloranil, bromanil, o-nitrobenzoic acid, trinitrofluorenone, quinone, benzoquinone, diphenoquinone, naphthoquinone, anthraquinone, and stilbenequinone can be used. In particular, the compounds represented by structural formulae ET1-1 to ET1-16, ET2-1 to ET2-16, ET3-1 to ET3-12, ET4-1 to ET4-32, ET5-1 to ET5-8, ET6-1 to ET6-50, ET7-1 to ET7-14, ET8-1 to ET8-6, ET9-1 to ET9-4, ET10-1 to ET10-32, ET11-1 to ET11-16, ET12-1 to ET12-16, ET13-1 to ET13-16, ET14-1 to ET14-16, ET15-1 to ET15-16, ET-1 to ET1-36, etc., disclosed in Japanese Patent Application Laid-open No. 2000-314969 are preferable. One of said electron acceptors/electron transport substances can be used, or two or more may be used in combination.

There are no particular limitations on the hole transport substance(s), but it is preferable to use a styryl compound. Note that in the present specification, a 'styryl compound' means a compound having the structure represented by the following formula.

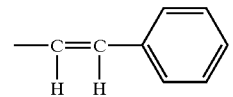

As specific structures of styryl compounds, examples include the compounds represented by structural formulae HT-1 to HT1-136 and HT2-1 to HT2-70 disclosed in Japanese Patent Application Laid-open No. 2000-314969, structural formulae V-40 to V-57 disclosed in Japanese Patent Application Laid-open No. 2000-204083, and structural formulae HT1-1 to HT1-70 disclosed in Japanese Patent Application Laid-open No. 2000-314970, although there is no limitation to said compounds in the present invention.

In addition, hydrazone compounds, pyrazoline compounds, pyrazolone compounds, oxadiazole compounds, oxazole compounds, arylamine compounds, benzidine compounds, stilbene compounds, polyvinylcarbazole compounds, polysilane compounds, etc., (for specific structures, see for example structural formulae HT3-1 to HT3-39, HT4-1 to HT4-20, HT5-1 to HT5-10, and HT-1 to HT-37 disclosed in Japanese Patent Application Laid-open No. 2000-314969) may be used as hole transport substances. One hole transport substance may be used, or two or more may be used in combination.

As examples of the resin binder of the charge transport layer, a polycarbonate resin, a polyester resin, a polyvinyl acetal resin, a polyvinyl butyral resin, a vinyl chloride resin, a vinyl acetate resin, polyethylene, polypropylene, polystyrene, an acrylic resin, a polyurethane resin, an epoxy resin, a melamine resin, a silicon type resin, a silicone resin, a polyamide resin, a polystyrene resin, a polyacetal resin, a polyarylate resin, a polysulfone resin, a methacrylic acid ester polymer, and a copolymer of the above may be used in a suitable combination. Particular examples are polycarbonates having as principal repeat units structural units represented by structural formulae BD1-1 to BD1-16 disclosed in Japanese Patent Application Laid-open No. 2000-314969. Moreover, in addition, polyester resins and polycarbonate resins having as principal repeat units one or more structural units represented by structural formulae BD-1 to BD-7 disclosed in Japanese Patent Application Laid-open No. 2000-314969 are preferable, and two or more of said resins may be may be used mixed together. Moreover, resins of the same type but having different molecular weights may be used mixed together. The content of the resin binder is 10 to 90 wt %, preferably 20 to 80 wt %, relative to the solid content of the charge transport layer.

The thickness of the charge transport layer is preferably in a range of 3 to 100 µm, more preferably 10 to 50 µm, to maintain a surface potential that is effective for practical use.

For a single layer type photosensitive layer, charge generation substance(s), charge transport substance(s) and a resin binder are used as principal components. As with the charge transport substance(s), it is necessary to use at least one compound of the present invention represented by above-mentioned general formula (I) as an electron transport substance, but other charge transport substance(s) may also be used together with compound (I) as in the case of the charge transport layer 3b described above. Regarding the charge generation substance(s), compound(s) such as those used in the charge generation layer 3a described above may be used. Moreover, regarding the resin binder as well, a resin binder like that used in the charge transport layer 3b r the charge generation layer 3a described above may be used.

The thickness of the single layer type photosensitive layer is preferably in a range of 3 to 100 µm, more preferably 10 to 50 µm, this being to maintain a surface potential that is effective for practical use.

Each of the photosensitive layers described above may contain a degradation preventing agent such as an antioxidant or a photostabilizer, to improve the environmental resistance and the stability with respect to harmful light. Examples of compounds used for such purposes include chromanol derivatives such as tocopherol and esterified compounds, polyallylalkane compounds, hydroquinone derivatives, ether compounds, diether compounds, benzophenone derivatives, benzotriazol derivatives, thioether compounds, phenylenediamine derivatives, phosphonic acid esters, phosphorous acid esters, phenol compounds, hindered phenol compounds, straight-chain amine compounds, cyclic amine compounds, and hindered amine compounds.

Moreover, the photosensitive layer may contain a leveling agent such as a silicone oil or a fluorinated oil, to improve the leveling of the formed film and bestowing lubricity.

Furthermore, to reduce the frictional coefficient, bestow lubricity, etc., fine particles of a metal oxide such as silicon oxide (silica), titanium oxide, zinc oxide, calcium oxide, aluminum oxide (alumina) or zirconium oxide, a metal sulfide such as barium sulfate and calcium sulfate, or a metal nitride such as silicon nitride or aluminum nitride, or particles of a fluororesin such as a tetrafluoroethylene resin, a fluorinated comb-like graft polymer resin or the like may be included.

Moreover, as necessary, other publicly known additives may be included, as long as the electrophotographic properties are not markedly impaired.

The protective layer 4 may be provided as necessary to improve the printing resistance, etc., and comprises a layer having a resin binder as a principal component, or an inorganic thin film of amorphous carbon, alumina or the like. As the resin binder, the resin binder used in the charge transport layer 3b described earlier, a three-dimensionally cross-linked resin such as a siloxane resin, or the like may be used. Moreover, to improve the electrical conductivity, reduce the frictional coefficient, or bestow lubricity, fine particles of a metal oxide such as silicon oxide (silica), titanium oxide, zinc oxide, calcium oxide, aluminum oxide (alumina) or zirconium oxide, a metal sulfide such as barium sulfate or calcium sulfate, or a metal nitride such as silicon nitride or aluminum nitride, or particles of a fluororesin such as a tetrafluoroethylene resin, a fluorinated comb-like graft polymer resin or the like may be included in the resin binder.

Moreover, to bestow charge transporting ability, a charge transport substance, electron acceptor or electron transport substance as used in the photosensitive layer described above, or a compound of the present invention may be included, and to improve the leveling of the formed film and bestow lubricity, a leveling agent such as a silicone oil or a fluorinated oil may be included.

Following is a detailed description of a method of forming the photoreceptor according to an embodiment of the present invention. In the case of forming the undercoat layer 2, the photosensitive layer 3 (charge generation layer 3a, charge transport layer 3b), and the protective layer 4 described above by application, one may dissolve/disperse the constituent materials described above in a suitable solvent to produce an application liquid, apply using a suitable application method, and then dry.

As the solvent, an alcohol such as methanol, ethanol, n-propanol, i-propanol, n-butanol or benzyl alcohol, a ketone such as acetone, MEK (methyl ethyl ketone), methyl isobutyl ketone or cyclohexanone, an amide such as DMF (dimethylformamide) or dimethylacetamide, a sulfoxide such as dimethylsulfoxide, a cyclic or straight-chain ether such as THF (tetrahydrofuran), dioxane, dioxolane, diethyl ether, methylcellosolve or ethylcellosolve, an ester such as methyl acetate, ethyl acetate or n-butyl acetate, an aliphatic halogenated hydrocarbon such as methylene chloride, chloroform, carbon tetrachloride, dichloroethylene or trichloroethylene, a mineral oil such as ligroin, an aromatic hydrocarbon such as benzene, toluene or xylene, an aromatic halogenated hydrocarbon such as chlorobenzene or dichlorobenzene, or the like can be used. Moreover, two or more of said solvents may be used mixed together.

As the dispersion/dissolution method for the above-mentioned application liquid, a publicly known method such as a paint shaker, a ball mill, a bead mill (sand grinder) such as a Dynomill, or ultrasonic dispersion may be used, and as the application method, a publicly known method such as an dip coating method, seal coating, a spraying method, bar coating or blade coating may be used.

Moreover, the drying temperature and the drying time in the above-mentioned drying may be set as appropriate in view of the type of solvent used, the manufacturing cost, etc., but preferably the drying temperature is set between room temperature and 200° C., and the drying time is set within a range between no less than 10 minutes and no more than 2 hours. More preferably, the drying temperature is in a range from the boiling point of the solvent to the boiling point of the solvent plus 80° C. Moreover, the drying is generally carried out at normal pressure or under reduced pressure, and in a still state or with air blowing.

The electrophotographic photoreceptor of the present invention may be used with publicly known electrophotographic processes, and is preferably used with ordinary electrophotographic processes including processes of charging, exposure, developing, transfer and fixing, and may be used in a copier, printer, fax or the like having said electrophotographic processes.

Here, as charging processes, in a positive charging process, the photoreceptor is charged to have a positive polarity, and in a negative charging process, the photoreceptor is charged to have a negative polarity. The photoreceptor of the present invention may be used with a negative charging process, but exhibits a particularly high sensitivity with a positive charging process, and hence is preferably used with a positive charging process.

With respect to charging devices for the charging process, non-contact charging devices may use a corotron or a scorotron, and other charging devices may have a roller shape or a brush shape and charge the photoreceptor by contacting (or coming very close to) the photoreceptor. The photoreceptor of the present invention may be used with a process using either type of charging device.

As the light source used in the exposure process, generally a light source having a wavelength range in which the photoreceptor is sensitive is used. White light from a halogen lamp, a fluorescent lamp or the like, laser light, LED light or the like is preferable. In particular, when using a phthalocyanine as a charge generation substance, LED light or semiconductor laser light around 600 to 800 nm is particularly preferable. Moreover, by using a transparent substrate as the substrate of the photoreceptor, even an internal exposure method may be used.

As developing processes, there are predominantly a dry developing method using a dry toner, and a liquid developing (wet developing) method using a liquid toner. The photoreceptor of the present invention may be used with either method. Note that in the case of the liquid developing method, it is preferable to adopt a publicly known technique such that components of the photoreceptor are not dissolved out into the solvent contained in the liquid toner.

Moreover, for the developing process, there are a reverse developing method in which the toner is developed at exposed parts, and a normal developing method in which the toner is developed at non-exposed parts. When using a phthalocyanine as a charge generation substance in particular, it is preferable to use the reverse developing method.

With respect to publicly known electrophotographic processes, electrophotographic processes may include a cleaning process after the transfer process to remove or disperse untransferred toner remaining on the photoreceptor, and cleaner-less electrophotographic processes may not include such a cleaning process. The photoreceptor of the present invention may be used with either type of process.

Moreover, with respect to publicly known electrophotographic processes, electrophotographic processes may include a process of removing charge through exposure with light after the transfer process to remove charge remaining on the photoreceptor and thus average out the surface potential, and electrophotographic processes that do not include such a charge removing process. The photoreceptor of the present invention may be used with either type of process.

Moreover, an electrophotographic apparatus of the present invention contains an electrophotographic photoreceptor according to the present invention as described above, and carries out a charging process through a positive charging process. With the electrophotographic apparatus of the present invention, there are no particular limitations regarding the constitution other than that of the charging process, and ordinary electrophotographic processes may be used as described above.

Following is a description of the present invention through examples.

SYNTHESIS EXAMPLE 1

Synthesis of Compound of Above-mentioned Specific Example I-21

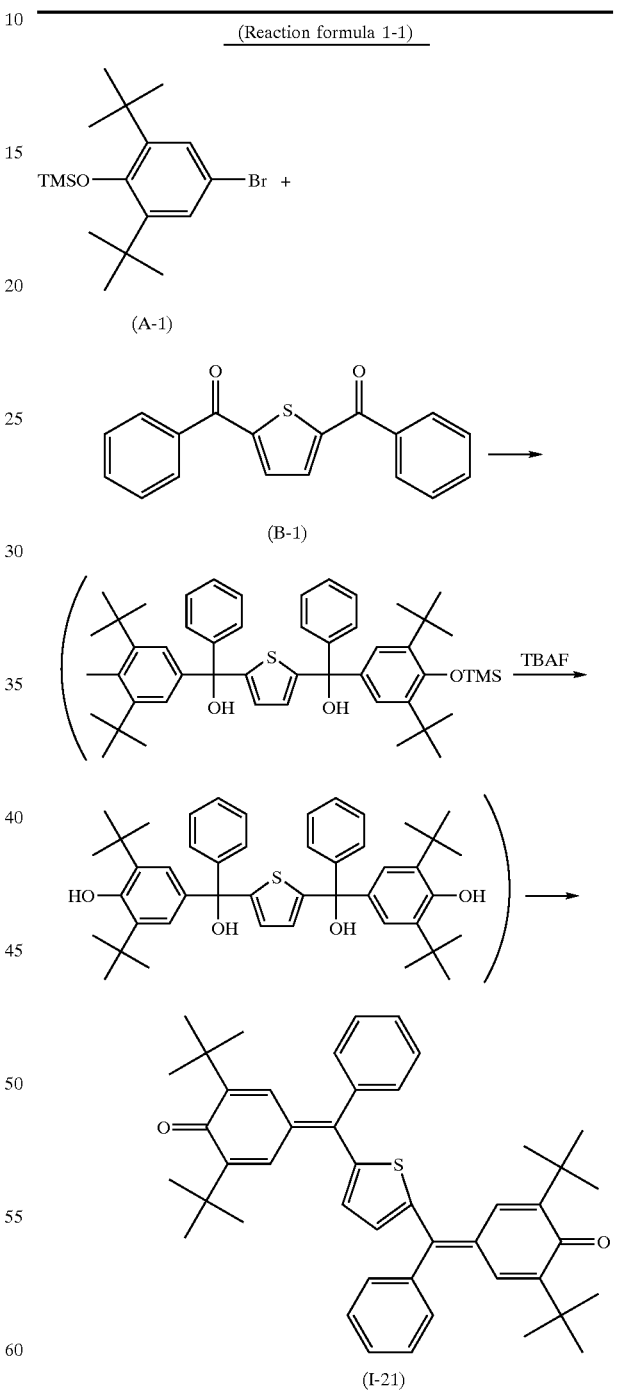

(Starting materials and reagents)

| | |
|---|---|
| 4-bromo-2,6-di-t-butyl-1-benzene (A-1) | 50 mmol (17.9 g) |
| THF (tetrahydrofuran) | 100 ml |
| n-butyl lithium (1.6M hexane solution) | 60 mmol (38 ml) |

-continued

| | |
|---|---|
| 2,5-dibenzoylthiophene (B-1) | 20 mmol (5.8 g) |
| THF (tetrahydrofuran) | 20 ml |
| Ammonium chloride aqueous solution | 10 ml |
| Tetrabutylammonium fluoride (TBAF) (1.0M THF solution) | 50 mmol (26.1 g) |
| p-toluenesulfonic acid monohydrate (p-TsOH) | Small amount |
| Toluene | 100 ml |

Method (1) The compound A-1 was weighed out into a 3-mouth flask, and THF (100 ml) was added.

(2) The n-butyl lithium was instilled in over 30 minutes under an $N_2$ atmosphere at −78° C. (dry ice-ethanol bath), and stirring was carried out for 30 minutes. A THF solution (20 ml) of the compound B-1 was then instilled in over 30 minutes under the same conditions, and stirring was carried out for 3 hours.

(3) Approximately 10 ml of saturated ammonium chloride aqueous solution was added, thus carrying out hydrolysis.

(4) The TBAF (50 ml) was added at 0° C. (ice bath), and stirring was carried out for 3 minutes.

(5) The reaction solution obtained was poured into ice water, and stirring was carried out.

(6) Extraction was carried out using dichloromethane, and then concentration was carried out.

(7) The solid component was dissolved in toluene (100 ml), a small amount of p-TsOH was added, and heating and refluxing were carried out for 2 hours.

(8) After the reaction had finished, concentration was carried out.

(9) The solid component was filtered off, and after washing with hexane, recrystallization was carried out using chloroform and ethanol.

Figure 5:
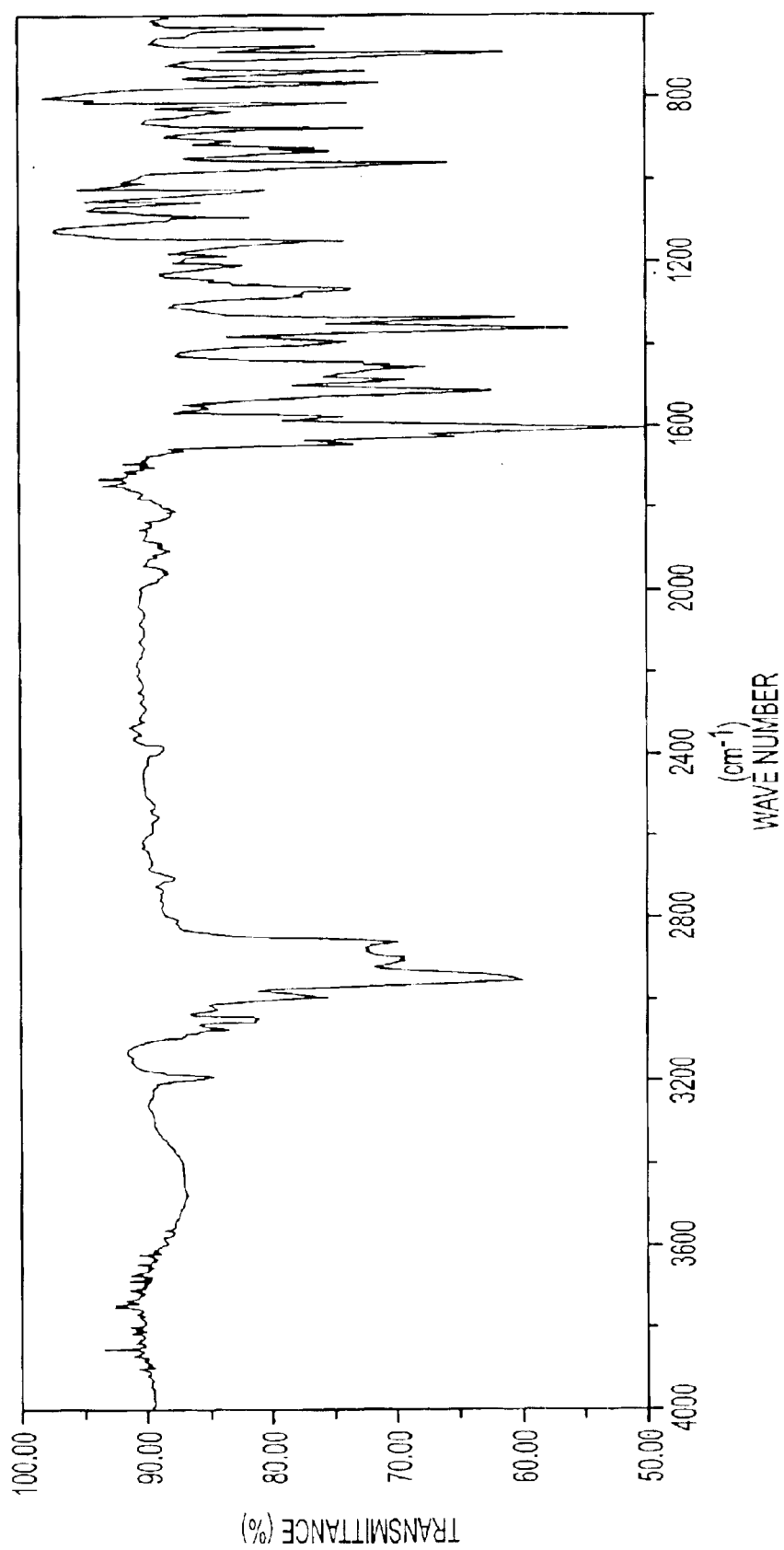
FIG. 5 is an IR spectrum of a compound represented by structural formula I-21.

As a result of the above, the compound represented by the above-mentioned formula I-21 was obtained. The yield was 8.0 g (59.8%), and the MS was m/z 669 ($M^+$). The IR spectrum of the compound of this specific example I-21 is shown in FIG. 5, and the $^1$H-NMR spectrum is shown in FIGS. 6A–6B.

SYNTHESIS EXAMPLE 2

Synthesis of Compound of Above-mentioned Specific Example I-51

(Reaction Formula 1-2)

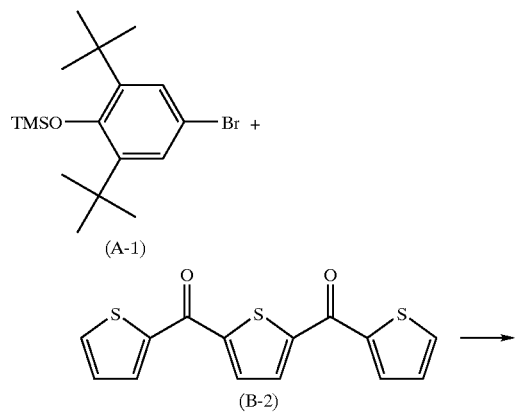

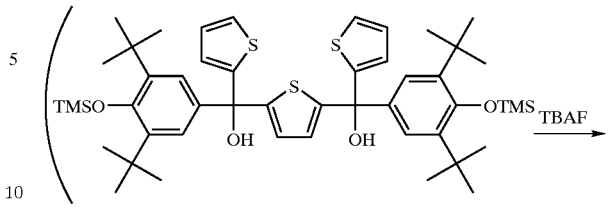

Figure 7:
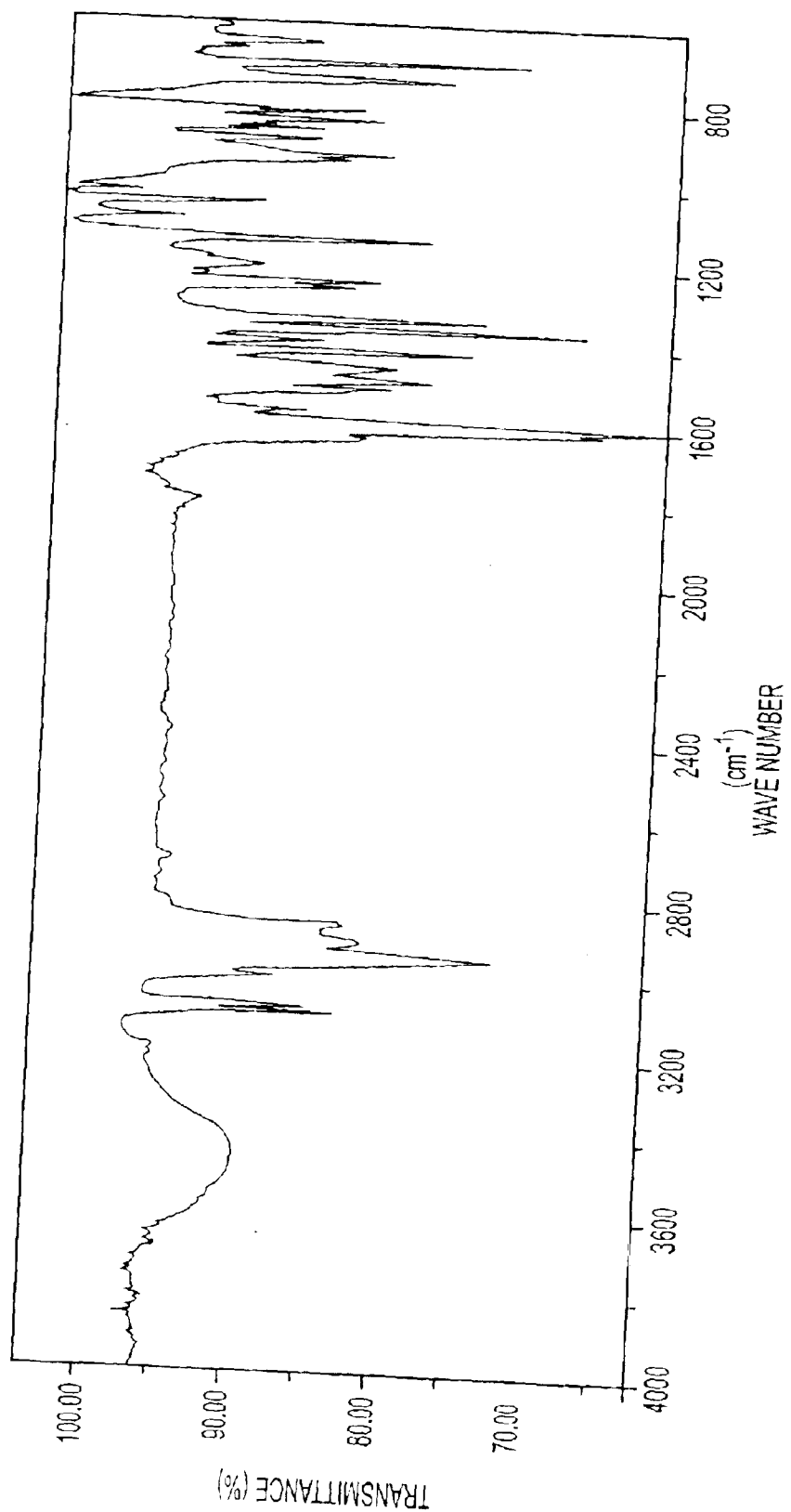
FIG. 7 is an IR spectrum of a compound represented by structural formula I-51.

The same method was carried out as in Synthesis Example 1, except that the 20 mmol (5.8 g) of 2,5-dibenzoylthiophene (B-1) used in Synthesis Example 1 was replaced with 20 mmol (6.1 g) of 2,5-dithenoylthiophene (B-2), whereby the compound represented by above-mentioned formula I-51 was obtained. The yield was 4.9 g (36.0%), and the MS was m/z 681 ($M^+$). The IR spectrum of the compound of formula I-51 is shown in FIG. 7, and the $^1$H-NMR spectrum is shown in FIGS. 8A–8B.

PHOTORECEPTOR EXAMPLE 1

A plate-shaped photoreceptor for evaluating electrical properties, and a drum-shaped photoreceptor (30 mm diameter) for evaluating printing were each produced.

An undercoat layer solution of the undermentioned composition was applied by dip coating onto each of an aluminum plate and an aluminum tube, and drying was carried out for 60 minutes at 100° C., thus forming an undercoat layer of thickness 0.3 μm. Note that in the following 'parts' means parts by weight.

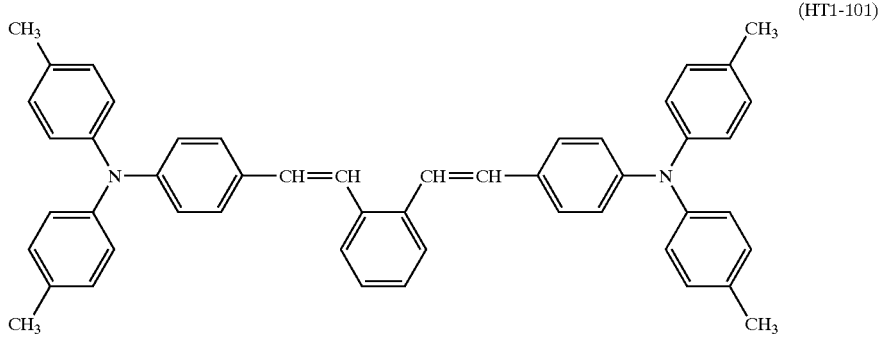

Next, a single layer type photosensitive layer dispersion of the below-mentioned composition was applied on by dip coating, and drying was carried out for 60 minutes at 100° C., thus forming a single layer type photosensitive layer of thickness 25 μm.
Charge generation substance: X-type non-metal phthalocyanine (see FIG. 2 in Japanese Patent Application Laid-open No. 2000-228637)
0.3 parts
Hole transport substance: Styryl compound represented by the below-mentioned structural formula HT1-101:

| | |
|---|---|
| Soluble nylon (AMILAN ™ CM8000; made by Toray Industries, Inc.) | 3 parts |
| Methanol/methylene chloride mixed solvent (5/5) | 97 parts |

| | |
|---|---|
| (HT1-101 in Japanese Patent Application Laid-open No. 2000-314969) | 7 parts |
| Electron transport substance: Compound represented by above-mentioned formula I-21 | 3 parts |
| Antioxidant: 3,5-di-tert-butyl-4-hydroxytoluene (BHT) (made by Tokyo Kasei Kogyo, Ltd.) | 1 part |
| Silicone oil: KF-50 (made by Shin-etsu Chemical Co., Ltd.) | 0.01 parts |
| Binder resin: Bisphenol Z-type polycarbonate resin (PANLITE ™ TS2020; made by Teijin Chemicals Ltd.) (BD1-1 in Japanese Patent Application Laid-open No. 2000-314969) | 10 parts |
| Methylene chloride | 100 parts |

By carrying out the above, electrophotographic photoreceptors were produced.

PHOTORECEPTOR EXAMPLE 2

Photoreceptors were produced as in Photoreceptor Example 1, except that, out of the composition of the photosensitive layer dispersion used in Photoreceptor Example 1, the 3 parts of the electron transport substance represented by above-mentioned formula I-21 were replaced with 3 parts of the electron transport substance represented by above-mentioned formula I-51.

PHOTORECEPTOR EXAMPLE 3

Photoreceptors were produced as in Photoreceptor Example 1, except that, out of the composition of the photosensitive layer dispersion used in Photoreceptor Example 1, the 3 parts of the electron transport substance represented by above-mentioned formula I-21 were replaced with 3 parts of the electron transport substance represented by above-mentioned formula I-28.

PHOTORECEPTOR EXAMPLE 4

Photoreceptors were produced as in Photoreceptor Example 1, except that, out of the composition of the photosensitive layer dispersion used in Photoreceptor Example 1, the 3 parts of the electron transport substance represented by above-mentioned formula I-21 were replaced with 3 parts of the electron transport substance represented by above-mentioned formula I-1.

PHOTORECEPTOR EXAMPLE 5

Photoreceptors were produced as in Photoreceptor Example 1, except that, out of the composition of the photosensitive layer dispersion used in Photoreceptor Example 1, as the hole transport substance the 7 parts of the styryl compound represented by above-mentioned formula HT1-101 were replaced with 7 parts of the styryl compound represented by the below-mentioned structural formula HT2-2:

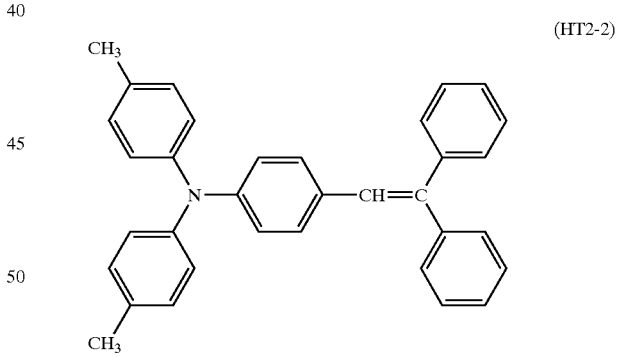

(HT2-2 in Japanese Patent Application Laid-open No. 2000-314969).

PHOTORECEPTOR EXAMPLE 6

Photoreceptors were produced as in Photoreceptor Example 1, except that, out of the composition of the photosensitive layer dispersion used in Photoreceptor Example 1, as the hole transport substance the 7 parts of the styryl compound represented by above-mentioned formula HT1-101 were replaced with 7 parts of the diamine compound represented by the below-mentioned structural formula HT-11:

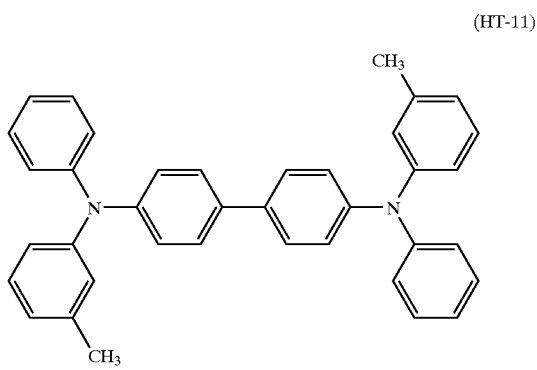

(HT-11)

(HT-11 in Japanese Patent Application Laid-open No. 2000-314969).

PHOTORECEPTOR EXAMPLE 7

Photoreceptors were produced as in Photoreceptor Example 1, except that, out of the composition of the photosensitive layer dispersion used in Photoreceptor Example 1, as the charge generation substance the 0.3 parts of the X-type non-metal phthalocyanine was replaced with 0.2 parts of an α-type titanyl phthalocyanine (see FIG. 3 in Japanese Patent Application Laid-open No. 2001-228637).

PHOTORECEPTOR EXAMPLE 8

Photoreceptors were produced as in Photoreceptor Example 1, except that, out of the composition of the photosensitive layer dispersion used in Photoreceptor Example 1, as the charge generation substance the 0.3 parts of the X-type non-metal phthalocyanine was replaced with 0.2 parts of a Y-type titanyl phthalocyanine (see FIG. 4 in Japanese Patent Application Laid-open No. 2001-228637).

PHOTORECEPTOR EXAMPLE 9

Photoreceptors were produced as in Photoreceptor Example 1, except that, out of the composition of the photosensitive layer dispersion used in Photoreceptor Example 1, as the charge generation substance the 0.3 parts of the X-type non-metal phthalocyanine was replaced with 0.2 parts of an amorphous titanyl phthalocyanine (see FIG. 5 in Japanese Patent Application Laid-open No. 2001-228637).

PHOTORECEPTOR EXAMPLE 10

Photoreceptors were produced as in Photoreceptor Example 1, except that, out of the composition of the photosensitive layer dispersion used in Photoreceptor Example 1, as the charge generation substance the 0.3 parts of the X-type non-metal phthalocyanine was replaced with 0.3 parts of the bisazo compound represented by the below-mentioned structural formula CG1-1:

PHOTORECEPTOR EXAMPLE 11

Photoreceptors were produced as in Photoreceptor Example 1, except that 0.3 parts of the bisazo compound represented by the above-mentioned structural formula CG1-1 was further added as an electron transport substance to the composition of the photosensitive layer dispersion used in Photoreceptor Example 1.

PHOTORECEPTOR COMPARATIVE EXAMPLE 1

Photoreceptors were produced as in Photoreceptor Example 1, except that, out of the composition of the photosensitive layer dispersion used in Photoreceptor Example 1, the 3 parts of the electron transport substance represented by above-mentioned formula I-21 replaced with 3 parts of the stilbenequinone compound represented by the below-mentioned structural formula (made by Tokyo Kasei Kogyo Co., Ltd.):

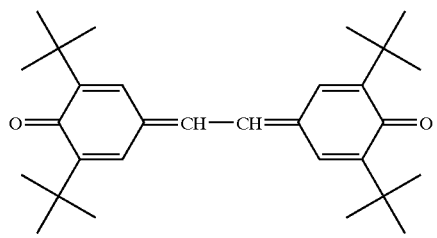

PHOTORECEPTOR COMPARATIVE EXAMPLE 2

Photoreceptors were produced as in Photoreceptor Example 1, except that, out of the composition of the photosensitive layer dispersion used in Photoreceptor Example 1, the 3 parts of the electron transport substance represented by above-mentioned formula I-21 was replaced with 3 parts of the diphenoquinone compound represented by the below-mentioned structural formula:

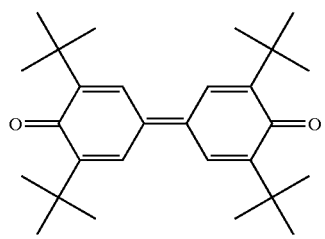

PHOTORECEPTOR COMPARATIVE EXAMPLE 3

Photoreceptors were produced as in Photoreceptor Example 1, except that the electron transport substance of

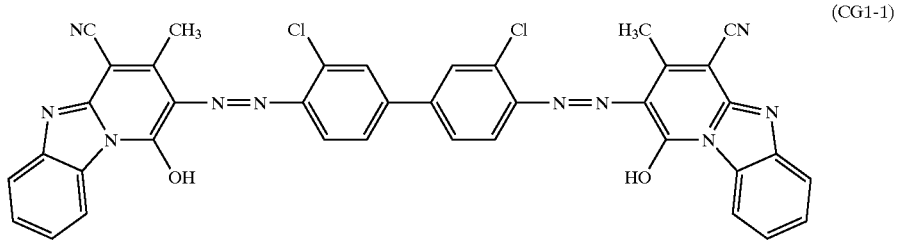

(CG1-1)

above-mentioned formula I-21 was not included in the composition of the photosensitive layer dispersion.

EVALUATION OF PHOTORECEPTOR EXAMPLES 1 TO 11 AND PHOTORECEPTOR COMPARATIVE EXAMPLES 1 TO 3

As the evaluation of electrical properties, using each of the plate-shaped photoreceptors, evaluation was carried out using an electrostatic copying paper testing apparatus EPA-8100 made by Kawaguchi Electric Works Co., Ltd.

Under an environment of a temperature of 23° C. and a humidity of 45%, charging was carried out in a dark place such that the surface potential became approximately +600V, and then the retention rate of the surface potential during a time period of 5 seconds until exposure with light was carried out was calculated from the following equation.

Retention rate $V_{k5}(\%) = (V_5/V_0) \times 100$ $V_0$: Surface potential immediately after charging
$V_5$: Surface potential after 5 seconds (when exposure with light commenced)

Next, the surface potential was similarly made to be +600 V, and exposure was carried out for 5 seconds with 1.0 $\mu W/cm^2$ monochromatic light of wavelength 780 nm (550 nm for Photoreceptor Example 10) that was produced from halogen lamp light using a filter; the exposure required for the surface potential to be halved (to +300 V) was obtained as the sensitivity $E_{1/2}(\mu J/cm^2)$, and the surface potential after the 5 seconds of exposure was obtained as the residual potential $V_r(V)$.

The evaluation results are shown in Table 1 below.

| | Retention Rate, $V_{k5}$ (%) | Sensitivity, $E_{1/2}$ ($\mu J/cm^2$) | Residual Potential, $V_r$ (V) |
|---|---|---|---|
| 1 | 84.3 | 0.36 | 48 |
| 2 | 81.2 | 0.39 | 51 |
| 3 | 86.4 | 0.34 | 45 |
| 4 | 84.7 | 0.40 | 71 |
| 5 | 88.5 | 0.39 | 45 |
| 6 | 79.7 | 0.48 | 59 |
| 7 | 80.2 | 0.34 | 44 |
| 8 | 81.3 | 0.35 | 42 |
| 9 | 88.0 | 0.37 | 53 |
| 10* | 89.3 | 0.49 | 55 |
| 11 | 81.0 | 0.33 | 42 |
| Comparative Example 1 | 82.7 | 0.57 | 117 |
| Comparative Example 2 | 78.2 | 0.55 | 105 |
| Comparative Example 3 | 89.7 | 0.59 | 158 |

*Exposed light: 550 nm

Moreover, as an evaluation of the durability upon actual printing, each drum-shaped photoreceptor was installed in an HL-1240 laser printer made by Brother Industries, Ltd., and a solid black image, a solid white image and a half-tone image were printed under an environment of a temperature of 22° C. and a humidity of 44%. An image of printing proportion approximately 5% was then printed 5000 times, and then a solid black image, a solid white image and a half-tone image were printed once again, and the images after printing 5000 times were evaluated.

The results were that for Photoreceptor Examples 1 to 9 and 11, good images were obtained for both the initial images and the images after printing 5000 times. On the other hand, for Photoreceptor Comparative Examples 1 to 3, the printing density was insufficient for the initial black image and half-tone image. Note that Photoreceptor Example 10 was unsuitable for the laser printer used due to not having sufficient sensitivity in the laser wavelength region (around 780 nm) of the laser printer utilized.

As described above, according to embodiments of the present invention, by using a compound having an excellent electron transporting ability as an electrophotographic photoreceptor, a high-durability electrophotographic photoreceptor having excellent electrical properties and stability even upon repeated use may be obtained; this electrophotographic photoreceptor is useful in electrophotographic apparatuses such as printers, copiers and faxes that use an electrophotographic method. In addition, the present invention may be embodied in a method of manufacturing and/or in an electrophotographic photoreceptor cartridge or drum attachable to/detachable from an image forming apparatus.

Although a few preferred embodiments of the present invention have been shown and described, it would be appreciated by those skilled in the art that changes may be made in this embodiment without departing from the principles and spirit of the invention, the scope of which is defined in the claims and their equivalents.

What is claimed is:

1. An electrophotographic photoreceptor, in which a photosensitive layer is provided on an electrically conductive substrate either directly or via an undercoat layer;
   wherein said photosensitive layer contains a compound having a structure represented by undermentioned general formula (I):

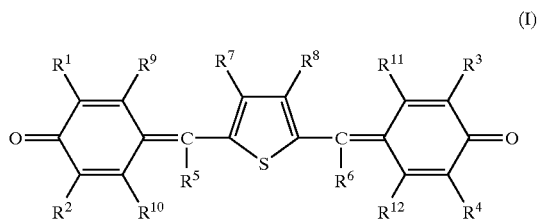

(I)

wherein $R^1$ to $R^4$ and $R^9$ to $R^{12}$ are the same or different and each represents a hydrogen atom, an optionally substituted alkyl group having 1 to 12 carbon atoms, an optionally substituted cyclic alkyl group, an optionally substituted aryl group, or an alkoxy group having 1 to 6 carbon atoms; $R^5$ and $R^8$ are the same or different and each represents a hydrogen atom, an optionally substituted alkyl group having 1 to 12 carbon atoms, an optionally substituted aryl group, or an optionally substituted heterocyclic group; $R^7$ and $R^8$ are the same or different and each represents a hydrogen atom, an optionally substituted alkyl group having 1 to 12 carbon atoms, an optionally substituted aryl group, or an alkoxy group having 1 to 6 carbon atoms; and each of the optional substituents is a halogen atom, an alkyl group having 1 to 6 carbon atoms, an alkoxy group having 1 to 6 carbon atoms, an aryl group, or a heterocyclic group.

2. The electrophotographic photoreceptor according to claim 1, wherein said photosensitive layer is a single layer type photosensitive layer.

3. The electrophotographic photoreceptor according to claim 1, wherein said photosensitive layer contains a styryl compound as a hole transport substance.

4. The electrophotographic photoreceptor according to claim 2, wherein said photosensitive layer contains a styryl compound as a hole transport substance.

5. The electrophotographic photoreceptor according to claim 1, wherein said photosensitive layer contains a phthalocyanine compound as a charge generation substance.

6. The electrophotographic photoreceptor according to claim 4, wherein said photosensitive layer contains a phthalocyanine compound as a charge generation substance.

7. An electrophotographic apparatus, which contains the electrophotographic photoreceptor according to claim 1, and carries out a charging process through a positive charging process.

8. An electrophotographic apparatus, which contains the electrophotographic photoreceptor according to claim 6 and carries out a charging process through a positive charging process.

9. A method of manufacturing an electrophotographic photoreceptor, comprising:
 providing a photosensitive layer on an electrically conductive substrate either directly or via an undercoat layer;
 wherein said photosensitive layer contains a compound having a structure represented by undermentioned general formula (I):

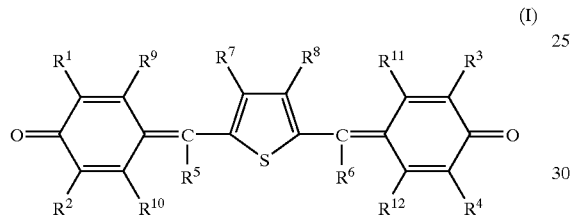

(I)

wherein $R^1$ to $R^4$ and $R^9$ to $R^{12}$ are the same or different and each represents a hydrogen atom, an optionally substituted alkyl group having 1 to 12 carbon atoms, an optionally substituted cyclic alkyl group, an optionally substituted aryl group, or an alkoxy group having 1 to 6 carbon atoms; $R^5$ and $R^8$ are the same or different and each represents a hydrogen atom, an optionally substituted alkyl group having 1 to 12 carbon atoms, an optionally substituted aryl group, or an optionally substituted heterocyclic group; $R^7$ and $R^8$ are the same or different and each represents a hydrogen atom, an optionally substituted alkyl group having 1 to 12 carbon atoms, an optionally substituted aryl group, or an alkoxy group having 1 to 6 carbon atoms; and each of the optional substituents is a halogen atom, an alkyl group having 1 to 6 carbon atoms, an alkoxy group having 1 to 6 carbon atoms, an aryl group, or a heterocyclic group, thereby forming a charge transport layer on a conductive support;
 dissolving a binder in an organic solvent selected from the group consisting of an alcoholic solvent, an acetate solvent, and a mixture of the alcoholic and acetate solvents, followed by the addition of a charge generating material, milling, dilution of the milled product with an alcoholic solvent, an acetate solvent, or a mixture of the alcoholic and acetate solvents, and mixing, to form a charge generating layer composition; and
 coating the charge generating layer composition on the charge transport layer and drying the charge generating layer composition to form a charge generating layer.

10. The method according to claim 9, wherein said photosensitive layer is a single layer type photosensitive layer.

11. The method according to claim 9, wherein said photosensitive layer contains a styryl compound as a hole transport substance.

12. The method according to claim 10, wherein said photosensitive layer contains a styryl compound as a hole transport substance.

13. The method according to claim 9, wherein said photosensitive layer contains a phthalocyanine compound as a charge generation substance.

14. The method according to claim 12, wherein said photosensitive layer contains a phthalocyanine compound as a charge generation substance.

15. An electrophotographic photoreceptor cartridge attachable to/detachable from an image forming apparatus, comprising:
 a positively-charged electrophotographic photoreceptor comprising
  a photosensitive charge transport layer on an electrically conductive substrate either directly or via an undercoat layer,
  wherein said photosensitive charge transport layer contains a compound having a structure represented by undermentioned general formula (I):

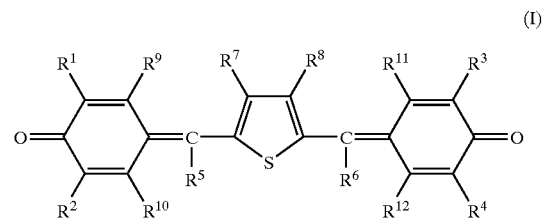

(I)

wherein $R^1$ to $R^4$ and $R^9$ to $R^{12}$ are the same or different and each represents a hydrogen atom, an optionally substituted alkyl group having 1 to 12 carbon atoms, an optionally substituted cyclic alkyl group, an optionally substituted aryl group, or an alkoxy group having 1 to 6 carbon atoms; $R^5$ and $R^6$ are the same or different and each represents a hydrogen atom, an optionally substituted alkyl group having 1 to 12 carbon atoms, an optionally substituted aryl group, or an optionally substituted heterocyclic group; $R^7$ and $R^8$ are the same or different and each represents a hydrogen atom, an optionally substituted alkyl group having 1 to 12 carbon atoms, an optionally substituted aryl group, or an alkoxy group having 1 to 6 carbon atoms; and each of the optional substituents is a halogen atom, an alkyl group having 1 to 6 carbon atoms, an alkoxy group having 1 to 6 carbon atoms, an aryl group, or a heterocyclic group to form the photosensitive charge transport layer on a conductive support; and
 a charge generating layer formed by dissolving a binder in an organic solvent selected from the group consisting of an alcoholic solvent, an acetate solvent, and a mixture of the alcoholic and acetate solvents, followed by the addition of a charge generating material, milling, dilution of the milled product with an alcoholic solvent, an acetate solvent, or a mixture of the alcoholic and acetate solvents, mixing to form a charge generating layer composition, coating the charge generating layer composition on the photosensitive charge transport layer and drying the charge generating layer composition to form a charge generating layer.

16. The electrophotographic photoreceptor according to claim 15, wherein said photosensitive layer is a single layer type photosensitive layer.

17. The electrophotographic photoreceptor cartridge according to claim 15, wherein said photosensitive layer contains a styryl compound as a hole transport substance.

18. The electrophotographic photoreceptor cartridge according to claim 16, wherein said photosensitive layer contains a styryl compound as a hole transport substance.

19. The electrophotographic photoreceptor cartridge according to claim 15, wherein said photosensitive layer contains a phthalocyanine compound as a charge generation substance.

20. The electrophotographic photoreceptor cartridge according to claim 18, wherein said photosensitive layer contains a phthalocyanine compound as a charge generation substance.

21. The electrophotoreceptor cartridge of claim 15, wherein the photosensitive layer contains, as a charge generation substance, at least one of: an X-type non-metal phthalocyanine, a-type titanyl phthalocyanine, and Y-type titanyl phthalocyanine.

22. An electrophotographic photoreceptor drum attachable to/detachable from an image forming apparatus, comprising:
a drum having a positively-charged electrophotographic photoreceptor installed thereon, the positively-charged electrophotographic photoreceptor comprising
a charge transport layer comprising a photosensitive layer on an electrically conductive substrate either directly or via an undercoat layer,
wherein said photosensitive layer contains a compound having a structure represented by undermentioned general formula (I):

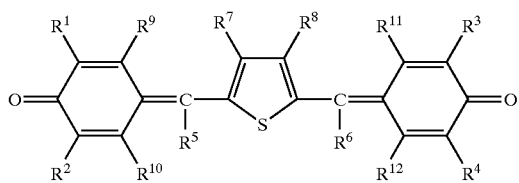

(I)

wherein $R^1$ to $R^4$ and $R^9$ to $R^{12}$ are the same or different and each represents a hydrogen atom, an optionally substituted alkyl group having 1 to 12 carbon atoms, an optionally substituted cyclic alkyl group, an optionally substituted aryl group, or an alkoxy group having 1 to 6 carbon atoms; $R^5$ and $R^6$ are the same or different and each represents a hydrogen atom, an optionally substituted alkyl group having 1 to 12 carbon atoms, an optionally substituted aryl group, or an optionally substituted heterocyclic group; $R^7$ and $R^8$ are the same or different and each represents a hydrogen atom, an optionally substituted alkyl group having 1 to 12 carbon atoms, an optionally substituted aryl group, or an alkoxy group having 1 to 6 carbon atoms; and each of the optional substituents is a halogen atom, an alkyl group having 1 to 6 carbon atoms, an alkoxy group having 1 to 6 carbon atoms, an aryl group, or a heterocyclic group forming the charge transport layer on a conductive support; and
a charge generating layer formed by dissolving a binder in an organic solvent selected from the group consisting of an alcoholic solvent, an acetate solvent, and a mixture of the alcoholic and acetate solvents, followed by the addition of a charge generating material, milling, dilution of the milled product with an alcoholic solvent, an acetate solvent, or a mixture of the alcoholic and acetate solvents, mixing to form a charge generating layer composition, coating the charge generating layer composition on the charge transport layer, and drying the charge generating layer composition to form the charge generating layer.

23. The electrophotographic photoreceptor drum according to claim 22, wherein said photosensitive layer is a single layer type photosensitive layer.

24. The electrophotographic photoreceptor drum according to claim 22, wherein said photosensitive layer contains a styryl compound as a hole transport substance.

25. The electrophotographic photoreceptor drum according to claim 23, wherein said photosensitive layer contains a styryl compound as a hole transport substance.

26. The electrophotographic photoreceptor drum according to claim 22, wherein said photosensitive layer contains a phthalocyanine compound as a charge generation substance.

27. The electrophotographic photoreceptor drum according to claim 25, wherein said photosensitive layer contains a phthalocyanine compound as a charge generation substance.

28. The electrophotographic photoreceptor drum of claim 22, wherein the photosensitive layer contains, as a charge generation substance, at least one of: an X-type non-metal phthalocyanine, α-type titanyl phthalocyanine, and Y-type titanyl phthalocyanine.

* * * * *

UNITED STATES PATENT AND TRADEMARK OFFICE
CERTIFICATE OF CORRECTION

PATENT NO. : 6,852,458 B2  
DATED : February 8, 2005  
INVENTOR(S) : Kenichi Ohkura et al.

Page 1 of 1

It is certified that error appears in the above-identified patent and that said Letters Patent is hereby corrected as shown below:

<u>Column 36,</u>  
Line 46, delete "$R^8$" and insert -- $R^6$ --.

<u>Column 37,</u>  
Line 39, delete "$R^8$" and insert -- $R^6$ --.

<u>Column 39,</u>  
Line 18, delete "a-type" and insert -- *a*-type --.

Signed and Sealed this

Second Day of May, 2006

JON W. DUDAS  
*Director of the United States Patent and Trademark Office*